(12) United States Patent
Stupp et al.

(10) Patent No.: US 7,534,761 B1
(45) Date of Patent: May 19, 2009

(54) CHARGED PEPTIDE-AMPHIPHILE SOLUTIONS AND SELF-ASSEMBLED PEPTIDE NANOFIBER NETWORKS FORMED THEREFROM

(75) Inventors: Samuel I. Stupp, Chicago, IL (US); Erik D. Spoerke, Evanston, IL (US); Shawn G. Anthony, New Stanton, PA (US); Krista L. Niece, Evanston, IL (US)

(73) Assignee: North Western University, Evanston, IL (US)

( * ) Notice: Subject to any disclaimer, the term of this patent is extended or adjusted under 35 U.S.C. 154(b) by 0 days.

(21) Appl. No.: 10/645,304

(22) Filed: Aug. 21, 2003

Related U.S. Application Data

(60) Provisional application No. 60/405,016, filed on Aug. 21, 2002.

(51) Int. Cl.
A01N 37/18 (2006.01)
A61K 38/00 (2006.01)

(52) U.S. Cl. .......................................... 514/2; 977/795
(58) Field of Classification Search ........................ None
See application file for complete search history.

(56) References Cited

U.S. PATENT DOCUMENTS

| | | | |
|---|---|---|---|
| 4,554,101 A | 11/1985 | Hopp | |
| 4,930,077 A | 5/1990 | Fan | |
| 5,130,123 A | 7/1992 | Reynolds et al. | |
| 5,208,111 A | 5/1993 | Decher et al. | |
| 5,670,483 A | 9/1997 | Zhang et al. | |
| 5,733,868 A | 3/1998 | Peterson et al. | |
| 5,843,780 A | 12/1998 | Thomson | |
| 5,871,767 A | 2/1999 | Dionne et al. | |
| 5,955,343 A | 9/1999 | Holmes et al. | |
| 5,993,541 A | 11/1999 | Litvin et al. | |
| 6,051,272 A | 4/2000 | Stupp et al. | |
| 6,085,206 A | 7/2000 | Domini et al. | |
| 6,096,863 A * | 8/2000 | Fields et al. | 530/326 |
| 6,156,321 A | 12/2000 | Thorpe et al. | |
| 6,181,909 B1 | 1/2001 | Burstein et al. | |
| 6,201,065 B1 | 3/2001 | Pathak et al. | |
| 6,265,539 B1 | 7/2001 | Arlinghaus | |
| 6,269,368 B1 | 7/2001 | Diamond | |
| 6,270,765 B1 | 8/2001 | Deo et al. | |
| 6,391,297 B1 | 5/2002 | Halvorsen | |
| 6,444,723 B1 | 9/2002 | Kline | |
| 6,458,924 B2 | 10/2002 | Knudsen et al. | |
| 6,473,730 B1 | 10/2002 | McKeown et al. | |
| 6,548,048 B1 | 4/2003 | Cuthbertson et al. | |
| 6,548,630 B1 | 4/2003 | Zhang et al. | |
| 6,562,619 B1 | 5/2003 | Gearhart et al. | |
| 6,800,481 B1 | 10/2004 | Holmes et al. | |
| 6,855,329 B1 | 2/2005 | Shakesheff et al. | |
| 6,890,654 B2 * | 5/2005 | Stupp et al. | 428/403 |
| 2002/0007217 A1 | 1/2002 | Jacob et al. | |
| 2002/0046018 A1 | 4/2002 | Marcu et al. | |
| 2002/0142277 A1 | 10/2002 | Burstein et al. | |
| 2002/0160471 A1 | 10/2002 | Kisiday et al. | |
| 2003/0059906 A1 | 3/2003 | Hubbell et al. | |
| 2003/0092672 A1 | 5/2003 | Darcy et al. | |
| 2003/0176335 A1 | 9/2003 | Zhang et al. | |
| 2004/0001893 A1 * | 1/2004 | Stupp et al. | 424/488 |
| 2004/0018961 A1 | 1/2004 | Stupp et al. | |
| 2004/0022718 A1 | 2/2004 | Stupp et al. | |
| 2004/0258726 A1 | 12/2004 | Stupp et al. | |
| 2005/0208589 A1 * | 9/2005 | Stupp et al. | 435/7.1 |
| 2005/0209145 A1 * | 9/2005 | Stupp et al. | 514/12 |
| 2005/0214257 A1 | 9/2005 | Zhao et al. | |
| 2005/0272662 A1 | 12/2005 | Stupp et al. | |
| 2006/0149036 A1 | 7/2006 | Stupp et al. | |
| 2006/0247165 A1 | 11/2006 | Stupp et al. | |

FOREIGN PATENT DOCUMENTS

| | | |
|---|---|---|
| JP | 03099096 A | 4/1991 |
| WO | WO 97/14713 A1 | 4/1997 |
| WO | WO 97/20639 A1 | 6/1997 |
| WO | WO 98/07752 * | 2/1998 |
| WO | 99/36107 | 7/1999 |
| WO | WO 00/13710 A2 | 3/2000 |
| WO | 00/45831 A1 | 8/2000 |
| WO | WO 00/44808 A1 | 8/2000 |
| WO | WO 00/52145 A2 | 9/2000 |

(Continued)

OTHER PUBLICATIONS

Sayle. Physiological ionization and pKa prediction. http://www.daylight.com/meetings/emug00/Sayle/pkapredic.html (accesed online Nov. 9, 2005), pp. 1-13.*

(Continued)

Primary Examiner—Cecilia J Tsang
Assistant Examiner—Marcela M Cordero Garcia

(57) ABSTRACT

The present invention provides a system of self-assembling peptide amphiphiles with an absolute net charge of 3 or greater whose design and function may be patterned after proteins involved in vertebrate mineralization or other tissue forming processes. This molecular system preferably consists of a hydrophobic hydrocarbon tail attached to a relatively hydrophilic peptide sequence. Self-assembly of this peptide amphiphile may be induced through pH variation, divalent ion addition, or dehydration. Variations of structural peptide sequences in the peptide amphiphile may enable the assembled nanofibers to be reversibly cross-linked for more or less structural stability, or may allow for control of the rate of self-assembly.

32 Claims, 11 Drawing Sheets

(3 of 11 Drawing Sheet(s) Filed in Color)

FOREIGN PATENT DOCUMENTS

| | | |
|---|---|---|
| WO | WO 00/64481 A1 | 11/2000 |
| WO | WO 01/00650 A1 | 1/2001 |
| WO | WO 02/062969 A2 | 8/2002 |
| WO | WO 03/040336 A2 | 5/2003 |
| WO | WO 03/054146 A2 | 7/2003 |
| WO | WO 03/070749 A2 | 8/2003 |
| WO | WO 03/084980 A2 | 10/2003 |
| WO | WO 03/090255 A2 | 10/2003 |
| WO | WO 2004/003561 A1 | 1/2004 |
| WO | WO 2004/018628 A2 | 3/2004 |
| WO | WO 2004/024778 A2 | 3/2004 |
| WO | WO 2004/046167 A2 | 6/2004 |
| WO | WO 2004/072104 A2 | 8/2004 |
| WO | WO 2004/106359 A2 | 12/2004 |
| WO | WO 2005/003292 A2 | 1/2005 |
| WO | WO 2005/056039 A1 | 6/2005 |
| WO | WO 2005/056576 A2 | 6/2005 |
| WO | WO 2006/096614 A2 | 9/2006 |

OTHER PUBLICATIONS

Hartgerink et al. Self-Assembly and Mineralization of Peptide-Amphiphile Nanofibers. Science. 2001. vol. 294, pp. 1684-1688.*

Murata et al. Membrane Fusion Induced by Mutual Interaction of the Two Charge-reversed Amphiphilic Peptides at Neutral pH. J Biol Chem. 1991. vol. 266, No. 2, pp. 14353-14358.*

Hartgerink et al. Peptide-amphiphile nanofibers: A versatile scaffold for the preparation of self-assembling materials. PNAS, 2002. vol. 99, No. 8, pp. 5133-5138.*

Yamada et al. Formation of Helical Super Structure From Single-Walled Bilayers by Amphiphiles with Oligo-L-Glutamic Acid-Head Group. Chemistry Letters. 1984, pp. 1713-1716.*

Forns et al. Induction of Protein-Like Molecular Architecture by Monoalkyl Hydrocarbon Chains. Biopolymers. 2000, vol. 54, pp. 531-546.*

Amino Acid Structures at Physiological pH accessed online at http://ww.brynmawr.edu/Acads/Chem/mnerzsto/amino_acids.htm,/amino_acids_2.gif and /amino_acids3.htm (3 pages).*

Torchilin. Structure and design of polymeric surfactant-based drug delivery systems. J Controlled Release. 2001. pp. 137-172.*

Fields et al. Proteinlike Molecular Architecture: Biomaterial Applications for Inducing Cellular Receptor Binding Signal Transduction. Biopolymers. 1998. vol. 47, pp. 143-151.*

Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similar Activities to the All-L-Peptide in Vitro and in Vivo." The Journal of Biological Chemistry. vol. 267, No. 20, pp. 14118-14121.

Margomenou-Leonidopoulou, G. 1994. "Thermotropic Mesophases of Ionic Amphiphiles. II. Ionic Amphiphiles in Aqueous Media." Journal of Thermal Analysis. vol. 42, pp. 1041-1061.

Rappolt, Michael and Gert Rapp. 1996. "Structure of the Stable and Metastable Ripple Phase of Dipalmitoylphosphatidylcholine." Eur. Biophys. J. vol. 24, pp. 381-386.

Goveas, J. L. and S. T. Milner. 1997. "Dynamics of the Lamellar—Cylindrical Transition in Weakly Segregated Diblock Copolymer Melts," Macromolecules. vol. 30, No. 9, pp. 2605-2612.

Munson, John B. and Stephen B. McMahon. 1997. "Effects of GDNF on Axotomized Sensory and Motor Neurons in Adult Rats." European Journal of Neuroscience. vol. 9, pp. 1126-1129.

Fernandez, A., M. A. Alsina, I. Haro, R. Galantai, and F. Reig. 1998. "Synthesis and Physicochemical Characterization of Cyclic Laminin Related Peptides." Langmuir. vol. 14, No. 13, pp. 3625-3630.

Yagi, Nobuhiro, Yoshikatsu Ogawa, Masato Kodaka, Tomoko Okada, Takenori TomohIro, Takeo Konakahara, and Hiroakl Okuno. 1999. "A Surface-Modified Functional Liposome Capable of Binding to Cell Membranes." Chem. Commun. pp. 1687-1688.

Luo, Yi and Glenn D. Prestwich. 2001. "Novel Biomaterials for Drug Delivery." Expert Opin. Ther. Patents. vol. 11, No. 9, pp. 1395-1410.

Marchl-Artzner, Valerie, Barbara Lorz, Ulrike Hellerer, Martin Kantlehner, Horst Kessler, and Erich Sackmann. 2001. "Selective Adhesion of Endothelial Cells to Artificial Membranes with a Synthetic RGD-Lipopeptide." Chem. Eur. J. vol. 7, No. 5, pp. 1095-1101.

Blight, Andrew R. Nov. 2002. "Miracles and Molecules—Progress in Spinal Cord Repair." Nature Neuroscience Supplement. vol. 5, pp. 1051-1054.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Niuvis Perez, and Michael J. Hannon. 2002. "Flow Oriented Linear Dichroism to Probe Protein Orientation in Membrane Environments." Phys. Chem. Chem. Phys. vol. 4, pp. 4051-4057.

Silva, G. A., K. L. Kehl, K. L. Niece, and S. I. Stupp. May 4, 2003. "Nanoengineered Peptide Amphiphile Network for Photoreceptor Replacement in Degenerative Retinal Disorders." Investigative Ophthalmology & Visual Science. Abstract No. 492 from Annual Meeting of the Association for Research in Vision and Opthalmology.

Brandenburg, Klaus, Frauke Wagner, Mareike Muller, Holger Heine, Jorg Andra, Michel H. J. Koch, Ulrich Zahringer, and Ulrich Seydel. 2003. "Physicochemical Characterization and Biological Activity of a Glycoglycerollpld from Mycoplasma formentans." Eur. J. Biochem. vol. 270, pp. 3271-3279.

Czeisler, C., V. M. Tysseling-Mattiace, G. A. Silva, S. I. Stupp, and J. A. Kessler. 2003. "Behavorial Improvement and Increased Survival Rate after Treatment with a Self Assembling Gel in a Rat Model of Spinal Cord Injury." 2003 Abstract Viewer/Itinerary Planner. Program No. 245.22. Washington, DC: Society for Neuroscience. Printed Feb. 5, 2007, p. 1. http://sfn.scholarone.com/itin2003/main.html?new_page_id=126&abstract_id=1554... .

Schmidt, Christine E. and Jennie Baier Leach. 2003. "Neural Tissue Engineering: Strategies for Repair and Regeneration." Annu. Rev. Biomed. Eng. vol. 5, pp. 293-347.

t' Hart, Bert A. and Sandra Amor. 2003. "The Use of Animal Models to Investigate the Pathogenesis of Neuroinflammatory Disorders of the Central Nervous System." Current Opinion in Neurology. vol. 16, pp. 375-383.

Beniash, Elia, Jeffery D. Hartgerink, Hannah Storrie, John C. Stendahl, and Samuel I. Stupp. 2005. "Self-Assembling Peptide Amphiphile Nanofiber Matrices for Cell Entrapment." Acta Biomaterialia. vol. 1, pp. 387-397.

Hoke, Ahmet. Aug. 2006. "Mechanisms of Disease: What Factors Limit the Success of Peripheral Nerve Regeneration in Humans?" Nature Clinical Practice Neurology. vol. 2, No.8, pp. 448-454.

Kokkoll, Efrosini, Anastasia Mardilovich, Alison Wedekind, Emilie L. Rexeisen, Ashish Garg, and Jennifer A. Craig. 2006. "Self-Assembly and Applications of Biomimetic and Bioactive Peptide-Amphiphiles." Soft Matter. vol. 2, pp. 1015-1024.

The LabRat.com. 2007, updated. Hank's Buffered Salt Solution (HBSS) Recipe. http://www.thelabrat.com/protocolsHanks.shtml. Printed Jan. 19, 2007. pp. 1-2.

U.S. Appl. No. 11/337,316, filed Jan. 23, 2006, Stupp et al.

Brown, Walter E. Dec. 15, 1962. "Octacalcium Phosphate and Hydroxyapatite." Nature. vol. 196. pp. 1048-1050.

Liang, W. Y. and A. D. Yoffe. Jan. 8, 1968. "Transmission Spectra of ZnO Single Crystals." Physical Review Letters. vol. 20, No. 2, pp. 59-62.

Greenfield, Norma and Gerald D. Fasman. Oct 1969. "Computed Circular Dichroism Spectra for the Evaluation of Protein Conformation." Biochemistry. vol. 8, No. 10, pp. 4108-4116.

Hantke, Klaus and Volkmar Braun. 1973. "Covalent Binding of Lipid to Protein: Diglyceride and Amide-Linked Fatty Acid at the N-Terminal End of the Murein-Lipoprotein of the *Escherichia coli* Outer Membrane." Eur. J. Biochem. vol. 34, No. 2, pp. 284-296.

Balcerski, James S., E. S. Pysh, G. M. Bonora, and C. Toniolo. Jun. 9, 1976. "Vacuum Ultraviolet Circular Dichroism of β-Forming Alkyl Oligopeptides." Journal of the American Chemical Society. vol. 98, No. 12, pp. 3470-3473.

Jacobson, Bruce S. and Daniel Branton. Jan. 21, 1977. "Plasma Membrane: Rapid Isolation and Exposure of the Cytoplasmic Surface by Use of Positively Charged Beads." Science. vol. 195, No. 4275, pp. 302-304.

Biesecker, G., J. Ieuan Harris, J. C. Thierry, J. E. Walker, and A. J. Wonacott. Mar. 24, 1977. *Nature*. vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." *Journal of the American Chemical Society*. vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formation." *Calcified Tissue International*. vol. 27, No. 1, pp. 75-82.

Richardson, P. M., U. M. McGuinness, and A. J. Aguayo. Mar. 20, 1980. "Axons from CNS Neurones Regenerate into PNS Grafts." *Nature*. vol. 284, pp. 264-265.

Lim, Franklin and Anthony M. Sun. Nov. 21, 1980. "Microencapsulated Islets as Bioartificial Endocrine Pancreas." *Science*. vol. 210, No. 4472, pp. 908-910.

Jain, Rakesh K., Chhitar M. Gupta, and Nitya Anand. 1981. "Synthesis of Peptidylglycophospholipids. Novel Derivatives of Muramyl-Dipeptide." *Tetrahedron Letters*. vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." *Analytical Biochemistry*. vol. 117, pp. 147-157.

Yannas, I. V., J. F. Burke, D. P. Orgill, E. M. Skrabut. Jan. 8, 1982. "Wound Tissue Can Utilize a Polymeric Template to Synthesize a Funtional Extension of Skin." *Science*. vol. 215, No. 4529, pp. 174-176.

Montesano, R., L. Orci, and P. Vassalli. Nov. 1983. "In Vitro Rapid Organization of Endothelial Cells into Capillary-like Networks Is Promoted by Collagen Matrices." *The Journal of Cell Biology*. vol. 97, pp. 1648-1652.

Pierschbacher, Michael D. and Erkki Ruoslahti. May 3, 1984. "Cell Attachment Activity of Fibronectin Can be Duplicated by Small Synthetic Fragments of the Molecule." *Nature*. vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest." *J. Vac. Sci. Technol*. vol. A 2, No. 2. pp. 1108-1111.

Thompson, Nancy L., Adrienne A. Brian, and Harden M. McConnell. 1984. "Covalent Linkage of a Synthetic Peptide to a Fluorescent Phospholipid and Its Incorporation into Supported Phospholipid Monolayers." *Biochimica et Biophysica Acta*. vol. 772, pp. 10-19.

Addadi, L. and S. Weiner. Jun. 15, 1985. "Interactions Between Acidic Proteins and Crystals: Stereochemical Requirements in Biomineralization." *Proceedings of the National Academy of Sciences of the United States of America*. vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters*. vol. 206, No. 2, pp. 262-266.

Mann, Stephen, John P. Hannington, and R. J. P. Williams. Dec. 11, 1986. "Phospholipid Vesicles as a Model System for Biomineralization." *Nature*. vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry*. vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research*. vol. 21, No. 12, pp. 1375-1381.

Bresnahan, J. C., M. S. Beattie, F. D. Tood III, and D. H. Noyes. 1987. "A Behavioral and Anatomical Analysis of Spinal Cord Injury Produced by a Feedback-Controlled Impaction Device." *Experimental Neurology*. vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Capillary Endothelial Cells." *Journal of Cellular Physiology*. vol. 131, pp. 123-130.

Lambert, Joseph B., Herbert F. Shurvell, David A. Lightner, and R. Graham Cooks. 1987. "Group Frequencies: Infrared and Raman." *Introduction to Organic Spectroscopy*. New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research*. No. 232, pp. 225-243.

Saksela Olli, David Moscatelli, Andreas Sommer, and Daniel B. Rifkin. Aug 1988. "Endothelial Cell-Drived Heparan Sulfate Binds Basic Fibroblast Growth Factor and Protects It from Proteolytic Degradation." *The Journal of Cell Biology*. vol. 107, pp. 743-751.

Cardin, Alan D. and H. J. R. Weintraub. Jan./Feb. 1989. "Molecular Modeling of Protein-Glycosaminoglycan Interactions." *Arteriosclerosis*. vol. 9, No. 1, pp. 21-32.

Oonishi, H., M. Yamamoto, H. Ishimaru, E. Tsuji, S. Kuskitani, M. Aono, and Y. Ukon. Mar. 1989. "The Effect of Hydroxyapatite Coating on Bone Growth into Porous Titanium Alloy Implants." *The Journal of Bone and Joint Surgery*. vol. 71-B, No. 2, pp. 213-216.

Friedmann, Theodore. Jun. 16, 1989. "Progress Toward Human Gene Therapy." *Science*. vol. 244, No. 4910, pp. 1275-1281.

Traub, Wolfie, Talmon Arad, and Stephen Weiner. Dec. 15, 1989. "Three-Dimensional Ordered Distribution of Crystals in Turkey Tendon Collagen Fibers." *Proceedings of the National Academy of Sciences of the United States of America*. vol. 86, No. 24, pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters*. vol. 30, No. 15, pp. 1927-1930.

Sambrook, Joseph, Edward F. Fritsch, and Thomas Maniatis. 1989. "Genes Encoding Selectable Markers." *Molecular Cloning: A Laboratory Manual*. 2$^{nd}$ ed. New York: Cold Spring Harbor Laboratory Press. pp. 16.9-16.15.

Veis, A. 1989. "Biochemical Studies of Vertebrate Tooth Mineralization." *Biomineralization*. S. Mann, J. Webb, and R. J. P. Williams, editors. Weinheim, Federal Republic of Germany: VCH Verlagsgesellschaft and New York: VCH Publishers. pp. 189-222.

Schnell, Lisa and Martin E. Schwab. Jan. 18, 1990. "Axonal Regeneration in the Rat Spinal Cord Produced by an Antibody Against Myelin-Associated Neurite Growth Inhibitors." *Nature*. vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery*. vol. 24, No. 1, pp. 17-23.

Van de Pol, Frans C. M. Dec. 1990. "Thin-Film ZnO—Properties and Applications." *Ceramic Bulletin*. vol. 69, No. 12, pp. 1959-1965.

Addadi, L., A. Berman, J. Moradian-Oldak, and S. Weiner. Dec. 28, 1990. "Tuning of Crystal Nucleation and Growth by Proteins: Molecular Interactions at Solid-Liquid Interfaces in Biomineralization." *Croatica Chemica Acta*. vol. 63, No. 3, pp. 539-544.

Sukenik, Chaim N., Natarajan Balachander, Lloyd A. Culp, Kristine Lewandowska, and Katherine Merritt. 1990. "Modulation of Cell Adhesion by Modification of Titanium Surfaces with Covalently Attached Self-Assembled Monolayers." *Journal of Biomedical Materials Research*. vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research*. vol. 4, No. 2, pp. 95-101.

Harris, Robin, Editor. 1991. *Electron Microscopy in Biology: A Practical Approach*. New York: Oxford University Press.

Jackson, David Y., David S. King. Jean Chmielewski, Sunil Singh, and Peter G. Schultz. 1991. "General Approach to the Synthesis of Short α-Helical Peptides." *Journal of the American Chemical Society*. vol. 113, pp. 9391-9392.

Polverini, Peter J., Noel P. Bouck, and Farzan Rastinejad. 1991. "Assay and Purification of Naturally Occurring Inhibitor of Angiogenesis." *Methods in Enzymology*. vol. 198, pp. 440-450.

Weiner, Stephen and Wolfie Traub. Feb. 1992. "Bone Structure: From Angstroms to Microns." *The FASEB Journal*. vol. 6, pp. 879-885.

Addadi, Lia and Stephen Weiner. 1992. "Control and Design Principles in Biological Mineralization." *Angew. Chem. Int. Ed. Engl*. vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science*. vol. 102, pp. 341. 351.

Cook, Stephen D., Kevin A. Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research*. vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry*. vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society*. vol. 114, No. 10, pp. 4000-4002.

Kunitake, Toyoki. 1992. "Synthetic Bilayer Membranes: Molecular Design, Self-Organization, and Application." *Angew. Chem. Int. Ed. Engl*. vol. 31, pp. 709-726.

Stupp, Samuel I. and Glenn W. Ciegler. 1992. "Organoapatites: Materials for Artificial Bone. I. Synthesis and Microstructure." *Journal of Biomedical Materials Research*. vol. 26, pp. 169-183.

Surewicz, Witold K., Henry H. Mantsch, and Dennis Chapman. Jan. 19, 1993. "Determination of Protein Secondary Structure by Fourier Transform Infrared Spectroscopy: A Critical Assessment." *Biochemistry*. vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic Membrane." *Proceedings of the National Academy of Sciences of the United States of America*. vol. 90, No. 8, pp. 3334-3338.

Langer, Robert and Joseph P. Vacanti. May 14, 1993. "Tissue Engineering." *Science*. vol. 260, No. 5110, pp. 920-926.

Mulligan, Richard C. May 14, 1993. "The Basic Science of Gene Therapy." *Science*. vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research*. vol. 72, No. 6, pp. 1005-1008.

Archibald, Douglas D. and Stephen Mann. Jul. 29, 1993. "Template Mineralization of Self-Assembled Anisotropic Lipid Microstructures." *Nature*. vol. 364, pp. 430-433.

Atala, Anthony, Linda G. Cima, Wooseob Kim, Keith T. Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology*. vol. 150, No. 2, pp. 745-747.

Ross-Murphy, S. B. and K. P. Shatwell. May-Aug. 1993. "Polysaccharide Strong and Weak Gels." *Biorheology*. vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Residues." *The Journal of Biological Chemistry*. vol. 268, No. 26, pp. 19228-19231.

Fowler, Bruce O., Milenko Marković, and Walter E. Brown. 1993. "Octacalcium Phosphate. 3. Infrared and Raman Vibrational Spectra." *Chem. Mater*. vol. 5, No. 10, pp. 1417-1423.

Fuhrhop, Jürgen-Hinrich, Dragan Spiroski, and Christoph Boettcher. 1993. "Molecular Monolayer Rods and Tubules Made of α-(L-Lysine),ω-(Amino) Bolaamphiphiles." *Journal of the American Chemical Society*. vol. 115, No. 4, pp. 1600-1601.

Graham, Stephan and Paul W. Brown. 1993. "The Low Temperature Formation of Octacalcium Phosphate." *Journal of Crystal Growth*. vol. 132, pp. 215-225.

Shimizu, Toshimi and Masakatsu Hato. 1993. "Self-Assembling Properties of Synthetic Peptidie Lipids." *Biochimica at Biophysica Acta*. vol. 1147, pp. 50-58.

Stupp, Samuel I., Jacqueline A. Hanson, Jo Ann Eurell, Glenn W. Ciegler, and Ann Johnson. 1993. "Organoapatites: Materials for Artificial Bone. III. Biological Testing." *Journal of Biomedical Materials Research*. vol. 27, pp. 301-311.

Stupp, Samuel I., George C. Mejicano, and Jacqueline A. Hanson. 1993. "Organoapatites: Materials for Artificial Bone. II. Hardening Reactions and Properties." *Journal of Biomedical Materials Research*. vol. 27, pp. 289-299.

Wald, Heidi L., Georgios Sarakinos, Michelle D. Lyman, Antonios G. Mikos, Joseph P. Vacanti, and Robert Langer. 1993. "Cell Seeding in Porous Transplantation Devices." *Biomaterials*. vol. 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth*. vol. 133, pp. 1-12.

Wang, B. C., T. M. Lee, E. Chang, and C. Y. Yang. 1993. "The Shear Strength and Failure Mode of Plasma-Sprayed Hydroxyapatite Coating to Bone: The Effect of Coating Thickness." *Journal of Biomedical Materials Research*. vol. 27, pp. 1315-1327.

San Antonio, James D., Arthur D. Lander, Morris J. Karnovsky, and Henry S. Slayter. Jun. 1994. "Mapping the Heparin-Binding Sites on Type I Collagen Monomers and Fibrils." *The Journal of Cell Biology*. vol. 125, No. 5, pp. 1179-1188.

Ban, S., S. Maruno, H. Iwata, and H. Itoh. 1994. "Calcium Phosphate Precipitation on the Surface of HA-G-Ti Composite Under Physiologic Conditions." *Journal of Biomedical Materials Research*. vol. 28, pp. 65-71.

de Bruijn, J. D., Y. P. Bovell, and C. A. van Blitterswijk. 1994. "Structural Arrangements at the Interface Between Plasma Sprayed Calcium Phosphates and Bone." *Biomaterials*. vol. 15, No. 7, pp. 543-550.

Hunter, Graeme K. and Harvey A. Goldberg. 1994. "Modulation of Crystal Formation by Bone Phosphoproteins: Role of Glutamic Acid-Rich Sequences in the Nucleation of Hydroxyapatite by Bone Sialoprotein." *Biochem. J*. vol. 302, pp. 175-179.

Klein, C. P. A. T., J. G. C. Wolke, J. M. A. de Blieck-Hogervorst, and K. de Groot. 1994. "Calcium Phosphate Plasma-Sprayed Coatings and Their Stability: An In Vivo Study." *Journal of Biomedical Materials Research*. vol. 28, pp. 909-917.

Mikos, Antonios G., Michelle D. Lyman, Lisa E. Freed, and Robert Langer. 1994. "Wetting of Poly(L-Lactic Acid) and Poly(DL-Lactic-co-glycolic Acid) Foams for Tissue Culture." *Biomaterials*. vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance*. vol. 4, No. 3, pp. 334-345.

Hubbell, Jeffrey A. Jun. 1995. "Biomaterials in Tissue Engineering." *Bio/technology*. vol. 13, pp. 565-576.

Fromm, J. R., R. E. Hileman. E. E. O. Caldwell, J. M. Weiler, and R. J. Linhardt. Nov. 10, 1995. "Differences in the Interaction of Heparin and Arginine and Lysine and the Importance of these Basic Amino Acids in the Binding of Heparin to Acidic Fibroblast Growth Factor." *Archives of Biochemistry and Biophysics*. vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve*. vol. 18, pp. 1417-1426.

Aletras, Alexios, Kleomenis Barlos, Dimitrios Gatos, Sophia Koutsogianni, and Petros Mamos. 1995, "Preparation of the Very Acid-Sensitive Fmoc-Lys(Mtt)-OH." *International Journal of Peptide & Protein Research*. vol. 45, pp. 488-496.

Berndt, Peter, Gregg B. Fields, and Matthew Tirrell. 1995. "Synthetic Lipidation of Peptides and Amino Acids: Monolayer Structure and Properties." *Journal of the American Chemical Society*. vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience*. vol. 18, pp. 159-192.

Nomizu, Motoyoshi, Benjamin S. Weeks, Christi A. Weston, Woo Hoo Kim, Hynda K. Kleinman, and Yoshihiko Yamada. 1995. "Structure-Activity Study of a Laminin α1 Chain Active Peptide Segment Ile-Lys-Val-Ala-Val (IKVAV)." *FEBS Letters*. vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of *mdx* Mice in Vitro and in Vivo ." *Tissue Engineering*. vol. 1, No. 4, pp. 327-343.

Sasanuma, Michio. 1995. "Optical Processes in ZnO." *J. Phys.: Condens. Matter*. vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials*. vol. 16, No. 18, pp. 1385-1393.

Falini, Guiseppe, Shira Albeck, Steve Weiner, and Lia Addadi. Jan. 5, 1996. "Control of Aragonite of Calcite Polymorphism by Mollusk Shell Macromolecules." *Science*. vol. 271, No. 5245, pp. 67-69.

Alivisatos, A. P. Feb. 16, 1996. "Semiconductor Clusters, Nanocrystals, and Quantum Dots." *Science*. vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor Is Critical for Its Mitogenic Potency." *The Journal of Biological Chemistry*. vol. 271, No. 13, pp. 7788-7795.

Belcher, A. M., X. H. Wu, R. J. Christensen, P. K. Hansma, G. D. Stucky, and D. E. Morse. May 2, 1996. "Control of Crystal Phase Switching and Orientation by Soluble Mulluse-Shell Proteins." *Nature*. vol. 381, pp. 56-58.

Hortelano, Gonzalo, Ayman Al-Hendy, Frederick A. Ofosu, and Patricia L. Chang. Jun. 15, 1996. "Delivery of Human Factor IX in Mice by Encapsulated Recombinant Myoblasts: A Novel Approach Towards Allogenic Gene Therapy of Hemophilia B." *Blood*. vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction." *J. Microencapsulation*. vol. 13, No. 4, pp. 363-375.

Alivisatos, A. Paul, Kai P. Johnsson, Xiaogang Peng, Troy E. Wilson, Colin J. Loweth, Marcel P. Burchez Jr., and Peter G. Schultz. Aug. 15, 1996. "'Organization of 'Nanocrystal Molecules' Using DNA," *Nature*. vol. 382, pp. 609-611.

George, Anne, Leslie Bannon, Boris Sabsay, Jerry W. Dillon, James Malone, Arthur Veis, Nancy A. Jenkins, Debra J. Gilbert, and Neal G. Copeland. Dec. 20, 1996. "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process." *The Journal of Biological Chemistry*. vol. 271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology*. vol. 139, pp. 244-256.

Burkett, Sandra L. and Stephen Mann. 1996. "Spatial Organization and Patterning of Gold Nanoparticles on Self-Assembled Biolipid Tubular Templates." *Chem. Commun*. pp. 321-322.

Hunter, Graeme K., Peter V. Hauschka, A. Robin Poole, Lawrence C. Rosenberg, and Harvey A. Goldberg. 1996. "Nucleation and Inhibition of Hydroxyapatite Formation by Mineralized Tissue Proteins." *Biochem. J*. vol. 317, pp. 59-64.

Karymov, Mikhail A., Karel Procházka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir*. vol. 12, No. 20, 4748-4753.

Landis, William J., Karen J. Hodgens, James Arena, Min Ja Song, and Bruce F. McEwen. 1996. "Structural Relations Between Collagen and Mineral in Bone as Determined by High Voltage Electron Microscopic Tomography." *Microscopy Research and Technique*. vol. 33, pp. 192-202.

Matsuzawa, Mieko, Forrest F. Weight, Richard S. Potember, and Påivi Liesi. 1996. "Directional Neurite Outgrowth and Axonal Differentiation of Embryonic Hippocampal Neurons Are Promoted by a Neurite Outgrowth Domain of the B2-Chain of Laminin." *Int. J. Devl. Neuroscience*. vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials*. vol. 17, No. 14, pp. 1417-1422.

Ratner, Buddy D., Allan S. Hoffman, Frederick J. Schoen, and Jack E. Lemons, Editors. 1996, *Biomaterials Science: An Introduction to Materials in Medicine*. San Diego, CA: Academic Press.

Ulman, Abraham. 1996. "Formation and Structure of Self-Assembled Monolayers." *Chemical Reviews*. vol. 96, No. 4, pp. 1533-1554.

Yu, Ying-Ching, Peter Berndt, Matthew Tirrell, and Gregg B. Fields. 1996. "Self-Assembling Amphiphiles for Construction of Protein Molecular Architecture." *Journal of the American Chemical Society*. vol. 118, No. 50, pp. 12515-12520.

Zarif, Leila, Ange Polidori, Bernard Pucci, Tadek Gulik-Krzywicki, André A. Pavia, and Jean G. Riess. 1996. "Effect of Chirality on the Formation of Tubules from Glycolipidic Amphiphiles," *Chemistry and Physics of Lipids*. vol. 79, pp. 165-170.

Aggeli, A., M. Bell, N. Boden, J. N. Keen, P. F. Knowles, T. C. B. McLeish, M. Pitkeathly, and S. E. Radford. Mar. 20, 1997. "Responsive Gels Formed by the Spontaneous Self-Assembly of Peptides into Polymeric β-Sheet Tapes." *Nature*. vol. 386, pp. 259-262.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry*. vol. 272, No. 26, pp. 16382-16389.

Dimmeler, Stefanie and Andreas M. Zeiher. Aug. 1997. "Nitric Oxide and Apoptosis: Another Paradigm for the Double-Edged Role of Nitric Oxide." *Nitric Oxide: Biology and Chemistry*. vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science*. vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimensional Culture System for Hepatocytes." *Cell Transplantation*. vol. 6, No. 5, pp. 463-468.

Aggeli, Amalia, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem*. vol. 7, No. 7, pp. 1135-1145.

Anderson, James M. and Matthew S. Shive. 1997. "Biodegradation and Biocompatibility of PLA and PLGA Microspheres." *Advanced Drug Delivery Reviews*. vol. 28, pp. 5-24.

Draget, Kurt Ingar, Gudmund Skjåk-Bræk, Olav Smidsrød. 1997. "Alginate Based New Materials." *International Journal of Biological Macromolecules*. vol. 21, pp. 47-55.

El-Ghannam, Ahmed, Paul Ducheyne, and Irving M. Shapiro. 1997. "Porous Bioactive Glass and Hydoxyapatite Ceramic Affect Bone Cell Function In Vitro Along Different Time Lines." *Journal of Biomedical Materials Research*. vol. 36, pp. 167-180.

Jaiswal, Neelam, Stephen E. Haynesworth, Arnold I. Caplan, and Scott P. Bruder. 1997. "Osteogenic Differentiation of Purified, Culture-Expanded Human Mesenchymal Stem Cells in Vitro." *Journal of Cellular Biochemistry*. vol. 64, pp. 295-312.

Nehrer, Stefan, Howard A. Breinan, Arun Ramappa, Sonya Shortkroff, Gretchen Young, Tom Minas, Clement B. Sledge, Ioannis V. Yannas, and Myron Spector. 1997. "Canine Chondrocytes Seeded in Type I and Type II Collagen Implants Investigated In Vitro." *Journal of Biomedical Materials Research (Appl. Biomater.)*. vol. 38, pp. 95-104.

Mann, Stephen. 1997. "Biomineralization: The Form(id)able Part of Bioinorganic Chemistry!" *J. Chem. Soc., Dalton Trans*. pp. 3953-3961.

Norrby, Klas. 1997. "Angiogenesis: New Aspects Relating to Its Initiation and Control." *APMIS*. vol. 105, pp. 417-437.

Shimizu, Toshimi, Masaki Kogiso, and Mitsutoshi Masuda. 1997. "Noncovalent Formation of Polyglycine II-Type Structure by Hexagonal Self-Assembly of Linear Polymolecular Chains." *Journal of the Americal Chemical Society*. vol. 119, No. 26, pp. 6209-6210, S2-S17.

Smith, George P. and Valery A. Petrenko. 1997. "Phage Display." *Chemical Reviews*. vol. 97, No. 2, pp. 391-410.

Toyotama, Akiko, Shin-ichi Kugimiya, Masakatsu Yonese, Takatoshi Kinoshita, and Yoshiharu Tsujita. 1997. "Controllable Orientation of the Peptide-Based Surfactant at Air-Water Interface." *Chemistry Letters*. pp. 443-444.

Weiner, Stephen and Lia Addadi. 1997. "Design Strategies in Mineralized Biological Materials." *J. Mater. Chem.* vol. 7, No. 5, pp. 689-702.

Wellings, Donald A. and Eric Atherton. 1997. "Standard Fmoc Protocols." *Methods in Enzymology*. vol. 289, pp. 44-67.

Wen, H. B., J. G. C. Wolke, J. R. de Wijn, Q. Liu, F. Z. Cui, and K. de Groot. 1997. "Fast Precipitation of Calcium Phosphate Layers on Titanium Induced by Simple Chemical Treatments." *Biomaterials*. vol. 18, No. 22, pp. 1471-1478.

Yu, Ying-Ching, Teika Pakalns, Yoav Dori, James B. McCarthy, Matthew Tirrell, and Gregg B. Fields. 1997. "Construction of Biologically Active Protein Molecular Architecture Using Self-Assembling Peptide-Amphiphiles." *Methods in Enzymology*. vol. 289, pp. 571-587.

Zhitomirsky, I. and L. Gal-Or. 1997. "Electrophoretic Deposition of Hydroxyapatite." *Journal of Materials Science: Materials in Medicine*. pp. 213-219.

Veis, Arthur, Kuiru Wei, Charles Sfeir, Anne George, and James Malone. Jan. 1998. "Properties of the (DSS)$_n$ Triplet Repeat Domain of Rat Dentin Phosphophoryn." *European Journal of Oral Sciences*. vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery*. vol. 42, No. 4, pp. 858-867.

Ogiso, M., Y. Yamashita, and T. Matsumoto. Jun. 1998. "The Process of Physical Weakening and Dissolution of the HA-Coated Implant in Bone and Soft Tissue." *Journal of Dental Research*. vol. 77, No. 6, pp. 1426-1434.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science*. vol. 281, No. 5375, pp. 389-392.

Orgill, Dennis P., Charles Butler, John F. Regan, Mark S. Barlow, I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery*. vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *Journal of the American Chemical Society*. vol. 120, No. 39, pp. 9979-9987.

Borkenhagen, M., J.-F. Clémence, H. Sigrist, and P. Aebischer. 1998. "Three-Dimensional Extracelluar Matrix Engineering in the Nervous System." *Journal of Biomedical Materials Research*. vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.)*. vol. 43, pp. 380-398.

Gu, Keni, Syweren R. Chang, Matt S. Slaven, Brian H. Clarkson, R. Bruce Rutherford, and Helena H. Ritchie. 1998. "Human Dentin Phosphophoryn Nucleotide and Amino Acid Sequence." *European Journal of Oral Sciences*. vol. 106, pp. 1043-1047.

Hartgerink, Jeffrey D., Thomas D. Clark, and M. Reza Ghadiri. 1998. "Peptide Nanotubes and Beyond." *Chem. Eur. J.* vol. 4, No. 8, pp. 1367-1372.

Johnstone, Brian, Thomas M. Hering, Arnold I. Caplan, Victor M. Goldberg, and Jung U. Yoo. 1998. "In Vitro Chondrogenesis of Bone Marrow-Derived Mesenchymal Progenitor Cells." *Experimental Cell Research*. vol. 238, pp. 265-272.

Kawasaki. M., A. Ohtomo, I. Ohkubo. H. Koinuma. Z. K. Tang, P. Yu, G. K. L. Wong. B. P. Zhang. and Y. Segawa. 1998. "Excitonic Ultraviolet Laser Emission at Room Temperature from Naturally Made Cavity in ZnO Nanocrytal Thin Films." *Materials Science and Engineering*. vol. B56, pp. 239-245.

Kogiso, Masaki, Satomi Ohnishi, Kiyoshi Yase, Mitsutoshi Masuda, and Toshimi Shimizu. 1998. "Dicarboxylic Oligopeptide Bolaamphiphiles: Proton-Triggered Self-Assembly of Microtubes with Loose Solid Surfaces." *Langmuir*. vol. 14, No. 18, pp. 4978-4986, S1-S7.

Kogiso, Masaki, Takeshi Hanada, Kiyoshi Yase, and Toshimi Shimizu. 1998. "Intralayer Hydrogen-Bond-Directed Self-Assembly of Nano-Fibers from Dicarboxylic Valylvaline Bolaamphiphiles." *Chem. Contm*. pp. 1791-1792.

Li, Panjian and Paul Ducheyne. 1998. "Quasi-Biological Apatite Film Induced by Titanium in a Simulated Body Fluid." *Journal of Biomedical Materials Research*. vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research*. vol. 40, pp. 324-335.

Tsui, Y. C., C. Doyle, and T. W. Clyne. 1998. "Plasma Sprayed Hydroxyapatite Coatings on Titanium Substrates Part 2: Optimisation of Coating Properties." *Biomaterials*. vol. 19, pp. 2031-2043.

Weiner, S. and H. D. Wagner. 1998. "The Material Bone: Structure-Mechanical Function Relations." *Annu. Rev. Mater. Sci.* vol. 28, pp. 271-298.

Wen, H. B., J. R. de Wijn, F. Z. Cui, and K. de Groot. 1998. "Preparation of Calcium Phosphate Coatings on Titanium Implant Materials by Simple Chemistry." *Journal of Biomedical Materials Research*. vol. 41, pp. 227-236.

Wheeler, Donna L., David L. Chamberland, John M. Schmitt, David C. Buck, John H. Brekke, Jeffrey O. Hollinger, S.-P. Joh, and K.-W. Suh. 1998. "Radiomorphometry and Biomechanical Assessment of Recombinant Human Bone Morphogenetic Protein 2 and Polymer in Rabbit Radius Ostectomy Model." *Journal of Biomedical Materials Research (Appl. Biomater.)*. vol. 43, pp. 365-373.

Wolke, J. G. C., K. de Groot, and J. A. Jansen. 1998. "In vivo Dissolution Behavior of Various RF Magnetron Sputtered Ca-P Coatings." *Journal of Biomedical Materials Research*. vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Surfaces." *Langmuir*. vol. 14, No. 19, pp. 5507-5516.

Xu, Guofeng, Nan Yao, IIhan A. Aksay, and John T. Groves. 1998. "Biomimetic Synthesis of Macroscopic-Scale Calcium Carbonate Thin Films, Evidence for a Multistep Assembly Process." *Journal of the American Chemical Society*. vol. 120, No. 46, pp. 11977-11985.

Yamada, Norihiro, Katsuhiko Ariga, Masanobu Naito, Kazuhiro Matsubara, and Emiko Koyama. 1998. "Regulation of β-Sheet Structures Within Amyloid-Like β-Sheet Assemblage from Tripeptide Derivatives." *Journal of the American Chemical Society*. vol. 120, No. 47, pp. 12192-12199.

Chusuei, Charles C., D. Wayne Goodman, Michael J. Van Stipdonk, Dina R. Justes, and Emile A. Schweikert. Jan. 1, 1999. "Calcium Phosphate Phase Identification Using XPS and Time-of-Flight Cluster SIMS." *Analytical Chemistry*. vol. 71, No. 1, pp. 149-153.

Zubarev, Eugene R., Martin U. Pralle, Leiming Li, and Samuel I. Stupp. Jan. 22, 1999. "Conversion of Supramolecular Clusters to Macromolecular Objects." *Science*. vol. 283, pp. 523-526.

Won, You-Yeon, H. Ted Davis, and Frank S. Bates. Feb. 12, 1999. "Giant Wormlike Rubber Micelles." *Science*. vol. 283, No. 5404, pp. 960-963.

Corral, Claudio J., Aamir Siddiqui, Liancun Wu, Catherine L. Farrell, David Lyons, and Thomas A. Mustoe. Feb. 1999. "Vascular Endothelial Growth Factor Is More Important Than Basic Fibroblastic Growth Factor During Ischemic Wound Healing." *Arch. Surg.* vol. 134, pp. 200-205.

Wheeler, B. C., J. M. Corey, G. J. Brewer, and D. W. Branch. Feb. 1999. "Microcontact Printing for Precise Control of Nerve Cell Growth in Culture." *Journal of Biomechanical Engineering*. vol. 121, pp. 73-78.

Cao, H., Y. G. Zhao, S. T. Ho. E. W. Seelig, Q. H. Wang, and R. P. H. Chang. Mar. 15, 1999. "Random Laser Action in Semiconductor Powder." *Physical Review Letters*. vol. 82, No. 11, pp. 2278-2281.

Aizenberg, Joanna, Andrew J. Black, and George M. Whitesides. Apr. 8, 1999. "Control of Crystal Nucleation of Patterned Self-Assembled Monolayers," *Nature*. vol. 398, pp. 495-498.

Niklason, L. E., J. Gao, W.M. Abbott, K. K. Hirschi, S. Houser, R. Marini, and R. Langer. Apr. 16, 1999. "Functional Arteries Grown in Vitro." *Science*. vol. 284, pp. 489-493.

Hahn, Junkseok and Stephen E. Webber. Apr. 1999. "Modification of Surfaces by Covalent Attachment of Polymer Micelles." *Macromolecular Symposia*. vol. 139, pp. 39-47.

Liu, Yi, Duckhyun Kim, B. Timothy Himes, Stella Y. Chow, Timothy Schallert, Marion Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *The Journal of Neuroscience*. vol. 19, No. 11, pp. 4370-4387.

Mehler, Mark F. and John A. Kessler. Jul. 1999. "Progenitor Cell Biology: Implications for Neural Regeneration." *Arch. Neurol*. vol. 56, pp. 780-784.

Tirrell, M. Oct. 27, 1999. "Biofunctionalization of Surfaces with Peptide Amphiphiles." *AVS: Science & Technology*. Invited Paper BI-WeM7.

McDonald, John W., Xiao-Zhong Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine*. vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation." *Chem. Mater*. vol. 11, No. 10, pp. 2694-2701.

Braun, Paul V. and Samuel I. Stupp. 1999. "CdS Mineralization of Hexagonal, Lamellar, and Cubic Lyotropic Liquid Crystals." *Materials Research Bulletin*. vol. 34, No. 3, pp. 463-469.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery*. vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine*. vol. 10, pp. 465-469.

Clark, Thomas D., Kenji Kobayashi, and M. Reza Ghadiri. 1999. "Covalent Capture and Stabilization of Cylindrical β-Sheet Peptide Assemblies." *Chem. Eur. J.* vol. 5, No. 2, pp. 782-792.

Cornish, J., K. E. Callon, C. Q.-X. Lin, C. L. Xiao, T. B. Mulvey, G. J. S. Cooper, and I. R. Reid. 1999. "Trifluoroacetate, a Contaminant in Purified Proteins, Inhibits Proliferation of Osteoblasts and Chondrocytes." *Am. J. Physiol. Endocrinol. Metab*. vol. 277, pp. 779-783.

Emoto, Kazunori, Yukio Nagasaki, and Kazunori Kataoka. 1999. "Coating of Surfaces with Stabilized Reactive Micelles from Poly-(ethylene glycol)—Poly(DL-Lactic Acid) Block Copolymer." *Langmuir*. vol. 15, No. 16, pp. 5212-5218.

Fields, Gregg B. 1999. "Induction of Protein-like Molecular Architecture by Self-Assembly Processes." *Bioorganic & Medicinal Chemistry*. vol. 7, pp. 75-81.

Haynes, Andrew J., Wei-Qun Huang, Jamie Mallah, Dajun Yang, Marc E. Lippman, and Lu-Yuan Li. 1999. "Angiopoietin-1 and Its Receptor Tie-2 Participate in the Regulation of Capillary-like Tubule Formation and Survival of Endothelial Cells." *Microvascular Research*. vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research*. vol. 47, pp. 504-515.

Ignjatović, Nenad, Simonida Tomić, Momčilo Dakić, Miroslav Miljković, Milenko Plavšić, and Dragan Uskoković. 1999. "Synthesis and Properties of Hydroxyapatite/Poly-L-Lactide Composite Biomaterials." *Biomaterials*. vol. 20, pp. 809-816.

Lee, Kevin J. and Thomas M. Jessell. 1999. "The Specification of Dorsal Cell Fates in the Vertebrate Central Nervous System." *Annual Review of Neuroscience*. vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir*. vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth*. vol. 206, pp. 308-321.

Miyaji, Fumiaki, Hyun-Min Kim, Shinichi Handa, Tadashi Kokubo, and Takashi Nakamura. 1999. "Bonelike Apatite Coating on Organic Polymers: Novel Nucleation Process Using Sodium Silicate Solution." *Biomaterials*. vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles in Self-Assembled Monolayer Films." *Biomaterials*. vol. 20, pp. 2265-2279.

Pittenger, Mark F., Alastair M. Mackay, Stephen C. Beck, Rama K. Jaiswal, Robin Douglas, Joseph D. Mosca, Mark A. Moorman, Donald W. Simonetti, Stewart Craig, and Daniel R. Marshak. Apr. 2, 1999. "Multilineage Potential of Adult Human Mesenchymal Stem Cells." *Science*. vol. 284, pp. 143-147.

Rezania, Alireza, Robert Johnson, Anthony R. Lefkow, and Kevin E. Healy. 1999. "Bioactivation of Metal Oxide Surfaces. 1. Surface Characterization and Cell Response." *Langmuir*. vol. 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials*. vol. 20, pp. 45-53.

Schense, Jason C. and Jeffrey A. Hubbell. 1999. "Cross-Linking Exogenous Bifunctional Peptides into Fibrin Gels with Factor XIIIa." *Bioconjugate Chem*. vol. 10, No. 1, pp. 75-81.

Varma, H. K., Y. Yokogawa, F. F. Espinosa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine*. vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research*. vol. 57, pp. 188-133.

Wei, M., A. J. Ruys, M. V. Swain, S. H. Kim, B. K. Milthorpe, and C. C. Sorrell. 1999. "Interfacial Bond Strength of Electrophoretically Deposited Hydroxyapatite Coatings on Metals." *Journal of Materials Science: Materials in Medicine*. vol. 10, pp. 401-409.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry*. vol. 38, No. 5, pp. 1659-1668.

Huq, N. Laila, Keith J. Cross, and Eric C. Reynolds. Feb. 4, 2000. "Molecular Modelling of a Multiphosphorylated Sequence Motif Bound to Hydroxyapatite Surfaces." *Journal of Molecular Modeling*. vol. 6, pp. 35-47.

Martinez, J. S., G. P. Zhang, P. D. Holt, H. -T. Jung, C. J. Carrano, M. G. Haygood, and Alison Butler. Feb. 18, 2000. "Self-Assembling Amphiphilic Siderophores from Marine Bacteria." *Science*. vol. 287, No. 5456, pp. 1245-1247.

Verrecchio, Angela, Markus W. Germann, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry*. vol. 275, No. 11, pp. 7701-7707.

Cao, H., J. Y. Xu, E. W. Seelig, and R. P. H. Chang. May 22, 2000. "Microlaser Made of Disordered Media." *Applied Physics Letters*. vol. 76, No. 21, pp. 2997-2999.

Marler, Jennifer J., Amrita Guha, Jonathan Rowley, Rahul Koka, David Mooney, Joseph Upton, and Joseph Vacanti. May 2000. "Soft-Tissue Augmentation with Injectable Alginate and Syngeneic Fibroblasts." *Plastic and Reconstructive Surgery*. vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America*. vol. 97, No. 12, pp. 6728-6733.

Whaley, Sandra R., D. S. English, Evelyn L. Hu, Paul F. Barbara, and Angela M. Belcher. Jun. 8, 2000. " Selection of Peptides with Semiconductor Binding Specificity for Directed Nanocrystal Assembly." *Nature*. vol. 405, pp. 665-668.

Sun, Xiu-xia and Chi-chen Wang. Jul. 28, 2000. "The N-Terminal Sequence (Residues 1-65) Is Essential for Dimerization, Activities, and Peptide Binding of *Escherichia coli* DsbC." *The Journal of Biological Chemistry*. vol. 275, No. 30, pp. 22743-22749.

Hsu, Wei-Cherng, Mark H. Spilker, Ioannis V. Yannas, and Peter A. D. Rubin. Aug. 2000. "Inhibition of Conjunctival Scarring and Contraction by a Porous Collagen-Glycosaminoglycan Implant." *Investigative Ophthalmology & Visual Science*. vol. 41, No. 9, pp. 2404-2411.

Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi. Sep. 2000. "Crystal Structure of a Ternary FGF-FGFR-Heparin Complex Reveals a Dual Role for Heparin in FGFR Binding and Dimerization." *Molecular Cell*. vol. 6, pp. 743-750.

Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters*. vol. 77, No. 15, pp. 2322-2324.

Schuldiner, Maya, Ofra Yanuka, Joseph Itskovitz-Eldor, Douglas A. Melton, and Nissim Benvenisly. Oct. 10, 2000. "Effects of Eight Growth Factors on the Differentiation of Cells Derived from Human Embryonic Stem Cells." *Proceedings of the National Academy of Sciences of the United States of America*. vol. 97, No. 21, pp. 11307-11312.

Altman, Michael, Peter Lee, Alexander Rich, and Shuguang Zhang. 2000, "Conformational Behavior of Ionic Self-Complementary Peptides." *Protein Science*. vol. 9, pp. 1095-1105.

Archer, Eric A., Noah T. Goldberg, Vincent Lynch, and Michael J. Krische. 2000. "Nanostructured Polymer Duplexes via the Covalent Casting of I-Dimensional H-Bonding Motifs: A New Strategy for the Self-Assembly of Macromolecular Precursors." *Journal of the American Chemical Society*. vol. 122, No. 20, pp. 5006-5007.

Ariga, Katsuhiko, Jun-ichi Kikuchi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound." *Langmuir*. vol. 16, No. 11, pp. 4929-4939.

Beniash, E., W. Traub, A. Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology*. vol. 132, pp. 212-225.

Bigi, Adriana, Elisa Boanini, Silvia Panzavolta, and Norberto Roveri. 2000. "Biomimetic Growth of Hydroxyapatite on Gelatin Films Doped with Sodium Polyacrylate." *Biomacromolecules*. vol. 1, No. 4, pp. 752-756.

Bourel, Line, Olivier Carion, Hélène Gras-Masse, and Oleg Melnyk. 2000. "The Deprotection of Lys(Mtt) Revisited." *Journal of Peptide Science*. vol. 6, pp. 264-270.

Caplan, Michael R., Peter N. Moore, Shuguang Zhang, Roger D. Kamm, and Douglas A. Lauffenburger. 2000. "Self-Assembly of a β-Sheet Protein Governed by Relief of Electrostatic Repulsion Relative to van der Waals Attraction." *Biomacromolecules*. vol. 1, No. 4, pp. 627-631.

Cardullo, F., M. Crego Calama, B. H. M. Snellink-Ruël, J.-L. Weidmann, A. Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun*. pp. 367-368.

Chamberlain, L. J., I. V. Yannas, H-P. Hsu, G. R. Strichartz, and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research*. vol. 60, pp. 666-677.

David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research*. vol. 6, No. 3, pp. 249-256.

Dori, Yoav, Havazelet Bianco-Peled, Sushil K. Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research*. vol. 50, pp. 75-81.

Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artifical Enzyme." *Colloids and Surfaces A: Physicochemical and Engineering Aspects*. vol. 169, pp. 143-153.

Kogiso, Masaki, Yuji Okada, Takeshi Hanada, Kiyoshi Yase, and Toshimi Shimizu. 2000. "Self-Assembled Peptide Fibers from Valylvaline Bola-Amphiphiles by Parallel β-Sheet Network." *Biochimica et Biophysica Acta*. vol. 1475, pp. 346-352.

Langer, Robert. 2000. "Biomaterials in Drug Delivery and Tissue Engineering: One Laboratory's Experience," *Accounts of Chemical Research*. vol. 33, No. 2, pp. 94-101.

Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction Is Regulated by Hemin." *J. Lab. Clin. Med*. vol. 136, No. 2, pp. 100-109.

Lu, Lichun, Susan J. Peter, Michelle D. Lyman, Hui-Lin Lai, Susan M. Leite, Janet A. Tamada, Shiro Uyama, Joseph P. Vacanti, Robert Langer, and Antonios G. Mikos. 2000. "In Vitro and In Vivo Degradation of Porous Poly(DL-Lactic-*co*-Glycolic Acid) Foams." *Biomaterials*. vol. 21, pp. 1837-1845.

Matsuura, T., R. Hosokawa, K. Okamoto, T. Kimoto, and Y. Akagawa. 2000. "Diverse Mechanisms of Osteoblast Spreading on Hydroxyapatite and Titanium." *Biomaterials*. vol. 21, pp. 1121-1127.

Ponticiello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research*. vol. 52, pp. 246-255.

Powell, Sharon K., Jayashree Rao, Eva Roque, Motoyoshi Nomizu, Yuichiro Kuratomi, Yoshihiko Yamada, and Hynda K. Kleinman. 2000. "Neural Cell Response to Multiple Novel Sites on Laminin-1." *Journal of Neuroscience Research*. vol. 61, pp. 302-312.

Sakiyama-Elbert, Shelly E. and Jeffrey A. Hubbell. 2000. "Controlled Release of Nerve Growth Factor from a Heparin-Containing Fibrin-Based Cell Ingrowth Matrix." *Journal of Controlled Release*. vol. 69, pp. 149-158.

Sakiyama-Elbert, Shelly E. and Jeffrey A. Hubbell. 2000. "Development of Fibrin Derivatives for Controlled Release of Heparin-Binding Growth Factors." *Journal of Controlled Release*. vol. 65, pp. 389-402.

Thareja, R. K. and A. Mitra. 2000. "Random Laser Action in ZnO." *Appl. Phys*. vol. B 71, pp. 181-184.

Tunggal, Patrick, Neil Smyth, Mats Paulsson, and Mark-Christoph Ott. 2000. "Laminins: Structure and Genetic Regulation." *Microscopy Research and Technique*. vol. 51, pp. 214-227.

do Serro, Ana Paula Valagān Amadeu, Anahela Catarino Fernandes, and Renilde de Jesus Vieira Saramago. 2000. "Calcium Phosphate Deposition on Titanium Surfaces in the Presence of Fibronectin." *Journal of Biomedical Materials Research*. vol. 49, pp. 345-352.

Yamada, Norihiro and Katsuhiko Ariga. 2000. "Formation of β-Sheet Assemblage with a View to Developing an Amyloid Model." *Synlett*. vol. 5, pp. 575-586.

Yang, Lin and Posohalis Alexandridis. 2000. "Physicochemical Aspects of Drug Delivery and Release from Polymer-Based Colloids." *Current Opinion in Colloid & Interface Science*. vol. 5, pp. 132-143.

Yu, Huanran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000. "Hydrophilicity of Polar and Apolar Domains of Amphiphiles." *Journal of Colloid and Interface Science*. vol. 229, pp. 375-390.

Zhu, G., M. F. Mehler, P. C. Mabie, and J. A. Kessler. 2000. "Development Changes in Neural Progenitor Cell Lineage Commitment Do Not Depend on Epidermal Growth Factor Receptor Signaling." *Journal of Neuroscience Research*. vol. 59, pp. 312-320.

Orlic, Donald, Jan Kajstura, Stefano Chimenti, Igor Jakonuk, Stacie M. Anderson, Baosheng Li, James Pickel, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature.* vol. 410, pp. 701-705.

Vailhé. Bruno, Daniel Vittet, and Jean-Jacques Feige. Apr. 2001. "In Vitro Models of Vasculogenesis and Angiogenesis." *Laboratory Investigation.* vol. 81, No. 4, pp. 439-452.

Davis, N. G., J. Teisen, C. Schuh, and D. C. Dunand. May 2001. "Solid-State Foaming of Titanium by Superplastic Expansion of Argon-Filled Pores." *J. Mater. Res.* vol. 16, No. 5, pp. 1508-1519.

Rabchevsky, Alexander G. and George M. Smith. May 2001. "Therapeutic Interventions Following Mammalian Spinal Cord Injury." *Arch. Neurol.* vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science.* vol. 292, pp. 1897-1899.

Lee, Kuen Yong and David J. Mooney. Jul. 2001. "Hydrogels for Tissue Engineering." *Chemical Reviews.* vol. 101, No. 7, pp. 1869-1879.

Aggeli, A., I. A. Nyrkova, M. Bell, R. Harding, L. Carrick, T. C. B. McLeish, A. N. Semenov, and N. Boden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America.* vol. 98, No. 21, pp. 11857-11862.

Richardson, Thomas P., Martin C. Peters, Alessandra B. Ennett, and David J. Mooney. Nov. 2001. "Polymeric System for Dual Growth Factor Delivery." *Nature Biotechnology.* vol. 19, pp. 1029-1034.

Mathew, Mathai and Shozo Takagi. Nov.-Dec. 2001. "Structures of Biological Minerals in Dental Research." *Journal of Research of the National Institute of Standards and Technology.* vol. 106, No. 6, pp. 1035-1044.

Woo, Byung Ho, Betsy F. Fink, Richard Page, Jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical Research.* vol. 18, No. 12, pp. 1747-1753.

Barrère, F., P. Layrolle, C. A. Van Blitterswijk, and K. de Groot. 2001. "Biomimetic Coatings on Titanium: A Crystal Growth Study of Octacalcium Phosphate." *Journal of Materials Science: Materials in Medicine.* vol. 12, pp. 529-534.

Bianco-Peled Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir.* vol. 17, No. 22, pp. 6931-6937.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science.* vol. 36, pp. 3253-3260.

Chang, John C., Gregory J. Brewer, and Bruce C. Wheeler. 2001. "Modulation of Neural Network Activity by Patterning." *Biosensors & Bioelectronics.* vol. 16, pp. 527-533.

Chang, Sophia C. N., Jon A. Rowley, Geoffrey Tobias Nicholas G. Genes, Amit K. Roy, David J. Mooney, Charles A. Vacanti and Lawrence J. Bonassar. 2001. "Injection Molding of Chondrocyte/Alginate Constructs in the Shape of Facial Implants." *Journal of Biomedical Materials Research.* vol. 55, pp. 503-511.

Doi, Tomokiyo, Takatoshi Kinoshita, Hiroki Kamiya, Shintaro Washizu, Yoshiharu Tsujita, and Hiraoki Yoshimizu. 2001. "Aggregation of Polypeptide-Based Amphiphiles in Water." *Polymer Journal.* vol. 33, No. 2, pp. 160-164.

Gore Tushar, Yoav Dori, Yeshayahu Talmon Matthew Tirrell, and Ilavazelet Bianco-Peled. 2001. "Self-Assembly of Model Collagen Peptide Amphiphiles." *Langmuir.* vol. 17, No. 17, pp. 5352-5360.

Hoess, Ronald H. 2001. "Protein Design and Phage Display." *Chemical Reviews.* vol. 101. No. 10. pp. 3205-3218.

Huang, Eric J. and Louis F. Reichardt. 2001. "Neurotrophins: Roles in Neuronal Development and Function." *Annual Review of Neuroscience.* vol. 24, pp. 677-736.

Kam, L., W. Shain, J. N. Turner, and R. Bizios. 2001. "Axonal Outgrowth of Hippocampal Neurons on Micro-Scale Networks of Polylysine-Conjugated Laminin." *Biomaterials.* vol. 22, pp. 1049-1054.

Kikuchi, Masanori, Soichiro Itoh, Shizuko Ichinose, Kenichi Shinomiya, and Junzo Tanaka. 2001. "Self-Organization Mechanism in a Bone-Like Hydoxyapatite/Collagen Nancomposite Synthesized in Vitro and Its Biological Reaction in Vivo." *Biomaterials.* vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research.* vol. 57, pp. 327-335.

Look, D. C. 2001. "Recent Advances in ZnO Materials and Devices." *Materials Science and Engineering.* vol. B80, pp. 383-387.

Matsui, Hiroshi, and Gary E. Douberly, Jr. 2001. "Organization of Peptide Nanotubes into Macroscopic Bundles." *Langmuir.* vol. 17, No. 25, pp. 7918-7922.

Neet, K. E. and R. B. Campenot. 2001. "Receptor Binding, Internalization, and Retrograde Transport of Neurotrophic Factors." *CMLS. Cell Mol. Life Sci.* vol. 58, pp. 1021-1035.

Otsuka, Hidenori, Yukio Nagasaki, and Kazunori Kataoka. 2001. "Self-Assembly of Poly(ethylene glycol)—based Block Copolymers for Biomedical Applications." *Current Opinion in Colloid & Interface Science.* vol 6, pp. 3-10.

Shimizu, Toshimi, Rika Iwaura, Mitsutoshi Masuda, Takeshi Hanada, and Kiyoshi Yase. 2001. "Internucleobase-Interaction-Directed Self-Assembly of the Nanofibers from Homo- and Heteroditopic 1,ω -Nucleobase Bolaamphiphiles." *Journal of the American Chemical Society.* vol. 123, No. 25, pp. 5947-5955, S1-S16.

Socrates, George. 2001. *Infrared and Raman Characteristic Group Frequencies: Tables and Charts.* Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir.* vol. 17, No. 3, pp. 866-872.

Takadama, Hiroaki, Hyun-Min Kim, Tadashi Kokubo, and Takashi Nakamura. 2001. " TEM-EDX Study of Mechanism of Bonelike Apatite Formation on Bioactive Titanium Metal in Simulated Body Fluid." *Journal of Biomedical Materials Research.* vol. 57, pp. 441-448.

Tanihara, Masao, Yasuo Suzuki, Eriko Yamamoto, Atsushi Noguchi, and Yutaka Mizushima. 2001. "Sustained Release of Basic Fibroblast Growth Factor and Angiogenesis in a Novel Covalently Crosslinked Gel of Heparin and Alginate." *Journal of Biomedical Materials Research.* vol. 56, pp. 216-221.

Yeung, C. K., L. Lauer, A. Offenhäusser, and W. Knoll. 2001. "Modulation of the Growth and Guidance of Rat Brain Stem Neurons Using Patterned Extracellular Matrix Proteins." *Neuroscience Letters.* vol. 301, pp. 147-150.

Zubarev, Eugene R., Martin U. Pralle, Eli D. Sone, and Samuel I. Stupp. 2001. "Self-Assembly of Dendron Rodcoil Molecules into Nanoribbons." *Journal of the American Chemical Society.* vol. 123, No. 17, pp. 4105-4106.

Hirschi, Karen K., Lihua Lai, Narasimhaswamy S. Belaguli, David A. Dean, Robert J. Schwartz, and Warren E. Zimmer. Feb. 22, 2002. "Transforming Growth Factorβ Induction of Smooth Muscle Cell Phenotype Requires Transcriptional and Post-transcriptional Control of Serum Response Factor." *The Journal of Biological Chemistry.* vol. 277, No. 8, pp. 6287-6295.

Xu, Weiming, Lizhi Liu, and Ian G. Charles. Feb. 2002. "Microencapsulated iNOS-expressing Cells Cause Tumor Suppression in Mice." *The FASEB Journal.* vol. 16, pp. 213-215.

Zubarev, Eugene R., Martin U. Pralle, Eli D. Sone, and Samuel I. Stupp. Feb. 2002. "Scaffolding of Polymers by Supramolecular Nanoribbons." *Advanced Materials.* vol. 14, No. 3, pp. 198-203.

Teng, Yang D., Erin B. Lavik, Xianlu Qu, Kook J. Park, Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells." *Proceedings of the National Academy of Sciences of the United States of America.* vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature*. vol. 416, pp. 636-640.

Vauthey, Sylvain, Steve Santoso, Haiyan Gong, Nicki Watson, and Shuguang Zhang. Apr. 16, 2002. "Molecular Self-Assembly of Surfactant-like Peptides to Form Nanotubes and Nanovesicles." *Proceedings of the National Academy of Sciences of the United States of America*. vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide Amphiphiles." *Nature*. vol. 417, pp. 424-428.

GrandPré, Tadzia, Shuxin Li, and Stephen M. Strittmatter. May 30, 2002. "Nogo-66 Receptor Antagonist Peptide Promotes Axonal Regeneration." *Nature*. vol. 417, pp. 547-551.

Storch, Alexander and Johannes Schwarz. May 2002. "Neural Stem Cells and Neurodegeneration." *Current Opinion in Investigational Drugs*. vol. 3, No. 5, pp. 774-781.

Lendlein, Andreas and Robert Langer. May 31, 2002. "Biodegradable, Elastic Shape-Memory Polymers for Potential Biomedical Applications." *Science*. vol. 296, pp. 1673-1676.

Qiu. Jin, Dongming Cai, Haining Dai, Marietta McAttee, Paul N. Hoffman, Barbara S. Bregman, and Marie T. Filbin. Jun. 13, 2002. "Spinal Axon Regeneration Induced by Elevation of Cyclic AMP." *Neuron*. vol. 34, pp. 895-903.

Catledge, Shane A., Marc D. Fries, Yogesh K. Vohra, William R. Lacefield, Jack E. Lemons, Shanna Woodard, and Ramakrishna Venugopalan. Jun.-Aug. 2002. "Nanostructured Ceramics for Biomedical Implants." *Journal of Nanoscience and Nanotechnology*. vol. 2, No. 3/4, pp. 293-312.

Alsberg, Eben, Kenneth W. Anderson, Amru Albeiruti, Jon A. Rowley, and David J. Mooney. Sep. 17, 2002, "Engineering Growing Tissues." *Proceedings of the National Academy of Sciences of the United States of America*. vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering*. vol. 8, No. 5, pp. 753-761.

Chang, Hua, Chester W. Brown, and Martin M. Matzuk. Dec. 2002. "Genetic Analysis of the Mammalian Transforming Growth Factor-β Superfamily." *Endocrine Reviews*. vol. 23, No. 6, pp. 787-823.

Busqué, Félix, Stephanie A. Hopkins, and Joseph P. Konopelski. 2002. "Progress Toward a Peptidomimetic of Laminin-Derived Pentapeptide YIGSR: Synthesis of the Unique Tricyclic Core Structure." *J. Org. Chem*. vol. 67, No. 17, pp. 6097-6103.

Canaple, Laurence, Annemie Rehor, and David Hunkeler. 2002. "Improving Cell Encapsulation Through Size Control." *J. Biomater. Sci. Polymer Edn*. vol. 13, No. 7, pp. 783-796.

Caplan, Michael R., Elissa M. Schwartzfarh, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials*. vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience*. vol. 20, pp. 125-139.

Cornish, Toby, Darren W. Branch, Bruce C. Wheeler, and James T. Campanelli. 2002. "Microcontact Printing: A Versatile Technique for the Study of Synaptogenic Molecules." *Molecular and Cellular Neuroscience*. vol. 20, pp. 140-153.

Costa, Silvia, Thierry Planchenault, Cecile Charriere-Bertrand, Yann Mouchel, Christiane Fages, Sharon Juliano, Thierry Lefrançois, Georgia Barlovatz-Meimon, and Marcienne Tardy. 2002. "Astroglial Permissivity for Neuritic Outgrowth in Neuron-Astrocyte Cocultures Depends on Regulation of Laminin Bioavailability." *GLIA*. vol. 37, pp. 105-113.

Gariépy, Jean, Sandrine Rémy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem*. vol. 13, No. 3, pp. 679-684.

Glättli, Alice, Xavier Daura, Dieter Seebach, and Wilfred F. van Gunsteren. 2002. "Can One Derive the Confrontational Preference of a β-Peptide from Its CD Spectrum?" *Journal of the American Chemical Society*. vol. 124, No. 44, pp. 12972-12978.

Gutwein, Luke G. and Thomas J. Webster. 2002. "Osteoblast and Chrondrocyte Proliferation in the Presence of Alumina and Titania Nanoparticles." *Journal of Nanoparticle Research*. vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Copolymeric Micelles to $TiO_2$ Surfaces." *Langniuir*. vol. 18, No. 1, pp. 252-258.

Issac, Roy and Jean Chmielewski. 2002. "Approaching Exponential Growth with a Self-Replicating Peptide." *Journal of the American Chemical Society*. vol. 124, No. 24, pp. 6808-6809.

Joshi, Mital and Michael G. Fehlings. 2002. "Development and Characterization of a Novel, Graded Model of Clip Compressive Spinal Cord Injury in the Mouse: Part 1. Clip Design, Behavioral Outcomes, and Histopathology." *Journal of Neurotrauma*. vol. 19, No. 2, pp. 175-190.

Joshi, Mital and Michael G. Fehlings. 2002. "Development and Characterization of a Novel, Graded Model of Clip Compressive Spinal Cord Injury in the Mouse: Part 2. Quantitative Neuroanatomical Assessment and Analysis of the Relationships Between Axonal Tracts, Residual Tissue, and Locomotor Recovery." *Journal of Neurotrauma*. vol. 19, No. 2, pp. 191-203.

Kruger, Ryan G., Patrick Dostal, and Dewey G. McCafferty. 2002. "An Economical and Preparative Orthogonal Solid Phase Synthesis of Fluorescein and Rhodamine Derivatized Peptides: FRET Substrates for the *Staphyococcus aureus* Sortase SrtA Transpeptidase Reaction." *Chem. Commun*. pp. 2092-2093.

Lauer, L., A. Vogt, C. K. Yeung, W. Knoll, and A. Offenhäusser. 2002. "Electrophysiological Recordings of Patterned Rat Brain Stem Slice Neurons." *Biomaterials*. vol. 23, pp. 3123-3130.

Lavik, Erin, Yang D. Teng, Evan Snyder, and Robert Langer. 2002. "Speeding Neural Stem Cells on Scaffolds and PGA, PLA, and Their Copolymers." *Methods in Molecular Biology: Neural Stem Cells: Methods and Protocols*. vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of a β-Sheet Peptide." *Nano Letters*. vol. 2, No. 4, pp. 295-299.

Ohsaki, Mio, Tatsuya Okuda, Akihiro Wada, Toshiya Hirayama, Takuro Niidome, and Haruhiko Aoyagi. 2002. "In Vitro Gene Transfection Using Dendritic Poly(L-lysine)." *Bioconjugate Chem*. vol. 13, No. 3, pp. 510-517.

Okano, Hideyuki. 2002. "Stem Cell Biology of the Central Nervous System." *Journal of Neuroscience Research*. vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telencephalon." *Molecular and Cellular Neuroscience*. vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials*. vol. 23, pp. 725-733.

Rowley, Jon A. and David J. Mooney. 2002. "Alginate Type and RGD Density Control Myoblast Phenotype." *Journal of Biomedical Materials Research*. vol. 60, pp. 217-223.

Santoso, Steve S., Sylvain Vauthey, and Shuguang Zhang. 2002. "Structures Function and Applications of Amphiphilic Peptides." *Current Opinion in Colloid & Interface Science*. vol. 7, pp. 262-266.

Thiébaud, Pierre, Lars Lauer, Wolfgang Knoll, and Andreas Offenhäuser. 2002. "PDMS Device for Patterned Application of Microfluids to Neuronal Cells Arranged by Microcontact Printing." *Biosensors & Bioelectronics*. vol. 17, pp. 87-93.

Tryoen-Tóth, Petra, Dominique Vautier, Youssef Haikel, Jean-Claude Voegel, Pierre Schaaf, Johanna Chluba, and Joëlle Ogier. 2002. "Viability, Adhesion, and Bone Phenotype of Osteoblast-like Cells on Polyelectrolyte Multilayer Films." *Journal of Biomedical Materials Research*. vol. 60, pp. 657-667.

Young, Wise. 2002. "Spinal Cord Contusion Models." *Progress in Brain Research*. vol. 137, pp. 231-255.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Mimetics of Collagenous Extracellular Matrices," *Nature Biotechnology*. vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery*. vol. 14, No. 3, pp. 308-316.

Cheng, Hongwei, Wei Jiang, Frank M. Phillips, Rex C. Haydon, Ying Peng, Lan Zhou, Hue H. Luu, Naili An, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPs)." *The Journal of Bone & Joint Surgery*. vol. 85-A, No. 8, pp. 1544-1552, 141.

Pavlov, Georges, Stéphanie Finet, Karine Tatarenko, Evgueniya Korneeva, and Christine Ebel. 2003. "Conformation of Heparin Studied with Macromolecular Hydrodynamic Methods and X-ray Scattering." *Eur. Biophys. J*. vol. 32, pp. 437-449.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone in a Critical-Sized Canine Segmental Defect." *The Journal of Bone & Joint Surgery*. vol. 85-A, No. 10, pp. 1927-1935.

Zhang, Shuguang. Oct. 2003. "Fabrication of Novel Biomaterials Through Molecular Self-Assembly." *Nature Biotechnology*. vol. 21, No. 10, pp. 1171-1178.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2002. "pH as a Trigger of Peptide β-Sheet Self-Assembly and Reversible Switching Between Nematic and Isotropic Phases." *Journal of the American Chemical Society*. vol. 125, No. 32, pp. 9619-9628.

Alsina, Jordi and Fernano Albericio. 2003. "Solid-Phase Synthesis of C-Terminal Modified Peptides." *Biopolymers (Peptide Science)*. vol. 71, pp. 454-477.

Anthony, Shawn G. 2003. "Injectable Biomaterials for Bone Tissue Engineering."

Boontheckul, Tanyarut and David J. Mooney. 2003. "Protein-Based Signaling Systems in Tissue Engineering." *Current Opinion in Biotechnology*. vol. 14, pp. 559-565.

Fauza, Dario O. 2003. "Tissue Engineering: Current State of Clinical Application." *Current Opinon in Pediatrics*. vol. 15, pp. 267-271.

Ganesh, S. and R. Jayakumar. 2003. "Structural Transitions Involved in a Novel Amyloid-Like β-Sheet Assemblage of Tripeptide Derivatives." *Biopolymers*. vol. 70, pp. 336-345.

Ganesh, S., S. Prakash, and R. Jayakumar. 2003. "Spectroscopic Investigation on Gel-Forming β-Sheet Assemblage of Peptide Derivatives." *Biopolymers*. vol. 70, pp. 346-354.

Gergely, C. S., P. Bar Yosef, R. Govrin-Lippman, F. Cuisinier, and H. Füredi-Milhofer. 2003. "The Deposition of Calcium Phosphates Within Polyelectrolyte Multilayer Films." *Key Engineering Materials*. vols. 240-242 (Bioceramics), pp. 287-290.

Goeden-Wood, Nichole L., Jay D. Keasling, and Susan J. Muller. 2003. "Self-Assembly of a Designed Protein Polymer into β-Sheet Fibrils and Responsive Gels." *Macromolecules*. vol. 36, No. 8, pp. 2932-2938.

Ishihara, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira Kurita. 2003. "Controlled Release of Fibroblast Growth Factors and Heparin from Photocrosslinked Chitosan Hydrogels and Subsequent Effect on in Vivo Vascularization." *Journal of Biomedical Materials Research*. vol. 64A, pp. 551-559.

Malkar, Navdeep B., Janelle L. Lauer-Fields, Darius Juska, and Gregg B. Fields. 2003. "Characterization of Peptide-Amphiphiles Possessing Cellular Activation Sequences." *Biomacromolecules*. vol. 4, No. 3, pp. 518-528.

Niece, Krista L., Jeffrey D. Hartgerink, Jack J. J. M. Donners, and Samuel I. Stupp. 2003. "Self-Assembly Combining Two Bioactive Peptide-Amphiphile Molecules into Nanofibers by Electrostatic Attraction." *Journal of the American Chemical Society*. vol. 125, No. 24, pp. 7146-7147.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology*. vol. 459, pp. 1-8.

Wu, Sufan, Yoshihisa Suzuki, Yoko Ejiri, Toru Noda, Hongliang Bai, Masaaki Kitada, Kazuya Kataoka, Masayoshi Ohta, Hirotomi Chou, and Chizuka Ide. 2003. "Bone Marrow Stromal Cells Enhance Differentiation of Cocultured Neurosphere Cells and Promote Regeneration of Injured Spinal Cord." *Journal of Neuroscience Research*. vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-Sheet Assembly." *Angew. Chem. Int. Ed*. vol. 42, pp. 5496-5499.

Zhang, Yan, Hongwei Gu, Zhimou Yang, and Bing Xu. 2003. "Supramolecular Hydrogels Respond to Ligand-Receptor Interaction." *Journal of American Chemical Society*. vol. 125, No. 45, pp. 13680-13681.

Hirano, Yoshiaki and David J. Mooney. Jan. 5, 2004. "Peptide and Protein Presenting Materials for Tissue Engineering." *Advanced Materials*. vol. 16, No. 1, pp. 17-25.

Silva, Gabriel A., Catherine Czeisler, Krista L. Niece, Elia Beniash, Daniel A. Harrington, John A. Kessler, and Samuel I. Stupp. Feb. 27, 2004. "Selective Differentiation of Neural Progenitor Cells by High-Epitope Density Nanofibers." *Science*. vol. 303, pp. 1352-1355.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience*. vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations and Permeability." *Circulation Research*. vol. 94, pp. 664-670.

Anthony, Shawn G. Mar. 28-Apr. 1, 2004. "Self-Assembling Nanofiber Matrix for Bone Regeneration." *The 227th ACS National Meeting*. Anaheim, CA.

Donners, Jack J. J. M. Mar. 28-Apr. 1, 2004. "Growth Factor Binding Self-Assembling Nanofiber Networks for Tissue Regeneration." *The 227th ACS National Meeting*. Anaheim, CA.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of America*. vol. 101, No. 23, pp. 8786-8790.

Pearse, Damien D., Francisco C. Pereira, Alexander E. Marcillo, Margaret L. Bates, Yerko A. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine*. vol. 10, No. 6. pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience*. vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings*. vol. 36, pp. 2464-2465.

Matsumura, Sachiko, Shinobu Uemura, and Hisakazu Mihara. 2004. "Fabrication of Nanofibers with Uniform Morphology by Self-Assembly of Designed Peptides." *Chem. Eur. J*. vol. 10, pp. 2789-2794.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research*. vol. 297, pp. 574-584.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience*. vol. 4, pp. 383-398.

Wang, Lin-Fa and Meng Yu. 2004. "Epitope Identification and Discovery Using Phage Display Libraries: Applications in Vaccine Development and Diagnostics." *Current Drug Targets*. vol. 5, No. 1, pp. 1-15.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters*. vol. 5, No. 1, pp. 1-4.

Guler, Mustafa O., Stephen Soukasene, James F. Hulvat, and Samuel I. Stupp. 2005. "Presentation and Recognition of Biotin on Nanofibers Formed by Branched Peptide Amphiphiles." *Nano Letters*. vol. 5, No. 2, pp. 249-252.

Copping, Aaron M. and Vanda R. G. Pond. Dec. 9, 1950. "Folic Acid as a Growth-Factor for the Rat." Nature. No. 4232, p. 993.

Mulloy, Barbara and Mark J. Forster. 2000. "Conformation and Dynamics of Heparin and Heparan Sulfate." Glycobiology. vol. 10, No. 11, pp. 1147-1156.

Bruggeman, Holger, Sebastian Baumer, Wolfgang Florian Fricke, Arnim Wiezer, Heiko Liesegang, Iwona Decker, Christina Herzberg, Rosa Martinez-Arias, Rainer Merkl, Anke Henne, and Gerhard Gottschalk. Feb. 4, 2003. "The Genome Sequence of Clostridium tetani, the Causative Agent of Tetanus Disease." PNAS. vol. 100, No. 3, pp. 1316-1321.

Invitrogen. Printed Jan. 22, 2008. "Dulbecco's Modified Eagle Medium (D-MEM) (1X) Liquid (High Glucose)." http://www.invitrogen.com/content.cfm?pageld=95&fuseaction=MediaForm.dsp_mediaForm&ProductId...

Uniprot entry for Q899Z6. Printed Mar. 14, 2008. http://www.pir.uniprot.org/cgi-bin/upEntry?id=Q899Z6_CLOTE. 3 pages.

Nomizu, Motoyoshi, Keizo Yamamura, Hynda K. Kleinman, and Yoshihiko Yamada. Aug. 1, 1993. "Multimeric Forms of Tyr-lle-Gly-Ser-Arg (YIGSR) Peptide Enhance the Inhibition of Tumor Growth and Metastasis." Cancer Research. vol. 53, pp. 3459-3461.

Jin, Young-Gu and K. J. Chang. Feb. 26, 2001. "Mechanism for the Enhanced Diffusion of Charged Oxygen Ions in SiO2." Physical Review Letters. vol. 86, No. 9, pp. 1793-1796.

Matsui, Hiroshi and Robert MacCuspie. Dec. 2001. "Metalloporphyrin Nanotube Fabrication Using Peptide Nanotubes as Templates." Nano Letters. vol. 1, No. 12, pp. 671-675.

Irvine, Darrell J. and Anne M. Mayes. 2001. "Nanoscale Clustering of RGD Peptides at Surfaces Using Comb Polymers. 1. Synthesis and Characterization of Comb Thin Films." Biomacromolecules. vol. 2, No. 1, pp. 85-94.

Matsui, Hiroshi, Precila Porrata, and Gary E. Douberly, Jr. 2001. "Protein Tubule Immobilization on Self-Assembled Monolayers on Au Substrates." Nano Letters. vol. 1, No. 9, pp. 461-464.

Slocik, Joseph M., Joshua T. Moore, and David W. Wright. Mar. 2002. Monoclonal Antibody Recognition of Histidine-Rich Peptide Encapsulated Nanoclusters. Nano Letters. vol. 2, No. 3, pp. 169-173.

Shih, Sheng-Ming, Wei-Fang Su, Yuh-Jiuan Lin, Cen-Shawn Wu, and Chii-Dong Chen. 2002. "Two-Dimensional Arrays of Self-Assembled Gold and Sulfur-Containing Fullerene Nanoparticles." Langmuir. vol. 18, No. 8, pp. 3332-3335.

Wong, Michael S., Jennifer N. Cha, Kyoung-Shin Choi, Timothy J. Deming, and Galen D. Stucky. 2002. "Assembly of Nanoparticles into Hollow Spheres Using Block Copolypeptides." Nano Letters. vol. 2, No. 6, pp. 583-587.

"AccessScience Search Results. Amphiphile." Accessed online May 7, 2007. http://www.accessscience.com/search/asearch?location=titlestext&newSearch=1&pubpriv=private&categories=dictionary&categval=dictionary&text=amphiphile. McGraw-Hill Encyclopedia of Science & Technology Online.

Jackowski, Andre. 1995. "Neural Injury Repair: Hope for the Future as Barriers to Effective CNS Regeneration Become Clearer." J. Neurosurg. vol. 9, pp. 303-317.

Knake, Rene, Amir W. Fahmi, Syed A. M. Tofail, Jason Clohessy, Miroslav Mihov, and Vincent J. Cunnane. 2005. "Electrochemical Nucleation of Gold Nanoparticles in a Polymer Film at a Liquid-Liquid Interface." Langmuir. vol. 21, No. 3, pp. 1001-1008.

\* cited by examiner

CHARGED PEPTIDE-AMPHIPHILE SOLUTIONS AND SELF-ASSEMBLED PEPTIDE NANOFIBER NETWORKS FORMED THEREFROM

CROSS REFERENCES TO RELATED APPLICATIONS

This application claims priority from U.S. Provisional Application Ser. No. 60/405,016 filed Aug. 21, 2002 the contents of which are incorporated herein by reference in their entirety.

GOVERNMENT INTEREST

The United States Government may have certain rights to this invention pursuant to Grant Nos.: DEFGO2-00ER45810; and DMRO 108342, from respectively the DOE and NSF to Northwestern University.

BACKGROUND OF THE INVENTION

One of the major difficulties of bone tissue engineering lies in mimicking the organo-mineral composites of natural bone. This is desirable since successful integration of an orthopedic implant into neighboring bony tissue would be characterized by the implant surface becoming part of the dynamic bone remodeling process. Implant surface features such as roughness and surface chemistry have been shown to play a critical role in osteoblastic differentiation and proliferation. Replicating natural bone is a challenge given its highly complex composition and organization. Natural bone can be thought of as an organo-mineral composite with seven levels of hierarchical organization, of which the basic building block is the mineralized collagen fibril. Each Type I collagen fibril is formed from self-assembly of three polypeptide chains into a triple helix. The principle mineral in bone, hydroxyapatite $(Ca_{10}(PO_4)_6OH_2)$, is believed to grow out of fibril channel gaps to form arrays of flat, nano-crystalline plates with their crystallographic c-axes aligned with the fibril long axes. It would be desirable to approach hard tissue engineering by patterning it after this biotemplating concept.

Titanium is valued for use in orthopedic surgery implants as a result of its excellent biocompatibility and mechanical properties, including high strength to weight ratio, toughness, and processibility. Titanium's surface is covered with a surface oxide layer that serves to give titanium its biocompatibility in vivo and makes titanium a relatively bioinert surface that does not elicit an immune or inflammatory response. It has been shown in the literature that coating this oxide surface with hydroxyapatite improves bone response and increases implant interfacial strength. It would be desirable to create a biomimetic hydroxyapatite organo-mineral material that would similarly elicit a favorable bone response.

Techniques of tissue engineering employing biocompatible scaffolds provide viable alternatives to prosthetic materials currently used in prosthetic and reconstructive surgery (e.g. craniomaxillofacial surgery). These materials also hold promise in the formation of tissue or organ equivalents to replace diseased, defective, or injured tissues. In addition to their use in the biocompatible scaffolds, biodegradable materials may be used for controlled release of therapeutic materials (e.g. genetic material, cells, hormones, drugs, or prodrugs) into a predetermined area. Most polymers used today to create these scaffolds, such as poly(lactic acid), polyorthoesters, and polyanhydrides, are difficult to mold and hydrophobic, resulting in, among other things, poor cell attachment and poor integration into the site where the tissue engineered material is utilized.

SUMMARY OF THE INVENTION

The present invention provides for self-assembling charged peptide amphiphiles whose design and function is patterned after proteins involved in vertebrate mineralization. The present invention is generally directed to the utilization of self-assembling molecules, more particularly highly charged self-assembling peptide amphiphiles to form such materials. Even more preferably, the present invention is directed to highly negatively charged self-assembling molecules to be utilized in tissue engineered material which enhance mineralization of the engineered material. In a preferred embodiment of the present invention self-assembly is utilized to form biocompatible material containing nanofiber networks.

One embodiment of the present invention is a peptide amphiphile composition. The peptide amphiphile's structure includes a hydrophobic component and a hydrophilic component, with the hydrophilic component having a net charge at physiological pH. The peptide amphiphile is further characterized in that-under suitable conditions it can be made to self assemble to form one or more micelles or micelles in the form of nanofibers. Under physiological conditions, the peptide-amphiphiles in the compositions may have a net positive charge or they may have a net negative charge. For negatively charged peptide amphiphiles, the negative net charge can be between −4 and −7, and may be −7 or more negative. The hydrophilic portion of the peptide amphiphile may include an amino acid is selected from the group consisting of serine, phosphorylated serine, diaminopropionic acid, and aspartic acid. The peptide component of the peptide-amphiphiles may also include an amino acid with a functional moiety capable of intermolecular covalent bond formation such as cysteine.

Another embodiment of the present invention is a peptide-amphiphile compound that includes an alkyl tail portion, a structural peptide portion and a functional peptide portion. The peptide amphiphile has a net charge at physiological pH. The peptide-amphiphile compound may have a net positive charge or it may have a negative net charge. Where the peptide amphiphile has a net negative charge, it can be between −4 and −7 or it may be more negative than −7. The functional peptide portion of the peptide amphiphile may include an amino acid selected from the group consisting of serine, phosphorylated serine, diaminopropionic acid, and aspartic acid. The structural peptide portion of the peptide amphiphile can include an amino acid with a functional moiety capable of intermolecular covalent bond formation such as cysteine.

One embodiment of the present invention is a composition that includes an aqueous solution of at least one peptide amphiphile and an agent for inducing said peptide amphiphiles to self assemble into a micelle or nanofiber. The peptide amphiphile is characterized in that it has a hydrophobic segment and a hydrophilic segment and a net charge at substantially physiological pH. The peptide amphiphile in the composition may have a net positive or a net negative charge. Where the net charge is negative, the charge on the peptide amphiphile can be from between −4 and −7, or the net charge of the peptide amphiphile can be more negative than −7.

Yet another embodiment of the present invention is a composition that includes peptide amphiphiles self assembled to form one or more micelles such as but not limited to nanofibers. The peptide amphiphiles have a hydrophobic segment and a hydrophilic segment and have a net charge at substantially physiological pH. The composition may also include a substrate with the self assembled peptide micelles covering at least a portion of the substrate.

One embodiment of the present invention is a method of treating a patient with tissue engineered material that includes administering a peptide amphiphile composition to a site on the patient in need of a tissue engineered material such as but not limited to bone, dentin, or an implant. The peptide amphiphile composition is capable of stimulating cell adhesion or mineralization at the site, and the peptide amphiphile in the composition has a net charge at physiological pH. The net charge on the peptide amphiphile in the composition may be positive or it may be negative. For negatively charged peptide amphiphiles the charge can be from between −4 and −7 or it can be −7 or more negative. The peptide-amphiphile in the composition administered to the site may include an amino acid selected from the group consisting of serine, phosphorylated serine, diaminopropionic acid, and aspartic acid. The peptide-amphiphile may also include an amino acid residue with a functional moiety capable of intermolecular covalent bond formation such as cysteine.

Another embodiment of the present invention is a mineralizable bone-defect filler composition comprised of a charged self assembling peptide-amphiphile compound. The charged peptide amphiphile includes an alkyl tail segment, a structural peptide segment, and a functional peptide segment and has a negative net charge at physiological pH. The mineralizable bone defect filler composition may also include cations and anions which are constituents of a mineral or substituted phases thereof. The peptide amphiphile in the mineralizable bone defect filler composition may have a net charge is between −4 and −7 or the net charge may be more negative than −7. The functional peptide segment of the peptide amphiphile may include an amino acid selected from the group consisting of serine, phosphorylated serine, diaminopropionic acid, and aspartic acid and the structural segment may include an amino acid with a function moiety capable of intermolecular covalent bond formation such as cysteine.

Embodiment of the present invention include the use of a self-assembling peptide amphiphile system to direct mineralization in a bulk gel and on a biologically compatible implant surfaces. Embodiments of the present invention include a method to achieve alignment of self assembled peptide amphiphile nanofibers on the biologically compatible implant surface through different drying techniques. By changing the relative concentrations of peptide amphiphile and the mineralization conditions, nucleation and inhibition of biological materials such as hydroxyapatite o- charged self assembled peptide amphiphiles is achieved.

One embodiment of the present invention provides charged peptide amphiphiles that are particularly suitable for interactions with charged ions. The peptide amphiphiles may be positively or negatively charged and preferably are charged under physiological pH conditions. The charged moieties may be used to induce self-assembly.

Another embodiment of the present invention provides a system of self-assembling peptide amphiphiles with high negative charge whose design and function is patterned after proteins involved in vertebrate mineralization. This peptide amphiphile and the molecular system formed therefrom generally consist of a hydrophobic hydrocarbon tail attached to a relatively hydrophilic peptide sequence. Self-assembly of this peptide amphiphile (PA) may be induced through pH variation, divalent ion addition, or dehydration (drying). Variations of structural peptide sequences in the peptide amphiphile may enable the assembled nanofibers or micelles to be reversibly cross-linked for more or less structural stability, they may allow for control of the rate of self-assembly, or the cross linking may be used to control the release of compounds from self assembled nanofibers.

BRIEF DESCRIPTION OF THE FIGURES

The file of this patent contains at least one drawing executed in color. Copies of this patent with color drawing(s) will be provided by the Patent and Trademark Office upon request and payment of necessary fee.

Various aspects and applications of the present invention will become apparent to the skilled artisan upon consideration of the brief description of the figures and the detailed description of the invention, which follows.

DETAILED DESCRIPTION OF THE INVENTION

Before the present compositions and methods are described, it is to be understood that this invention is not limited to the particular molecules, compositions, methodologies or protocols described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of the present invention, the preferred methods, devices, and materials are now described. All publications mentioned herein are incorporated herein by reference. Nothing herein is to be construed as an admission that the invention is not entitled to antedate such disclosure by virtue of prior invention.

Figure 1A:
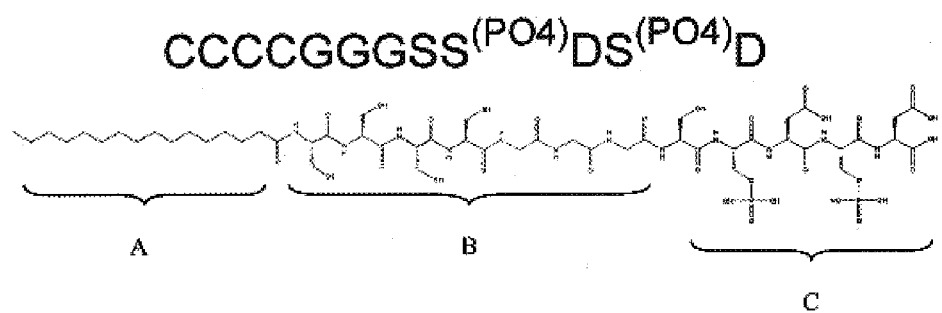
FIG. 1A illustrates the chemical structure of a negatively charged peptide-amphiphile that may be considered a platform for preferred embodiments of the present application (SEQ ID NO:1)
Figure 1B:
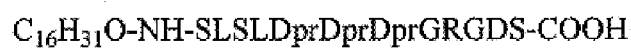
FIG. 1B illustrates the chemical structure of a positively charged peptide-amphiphile of the present invention (SEQ ID NO:22)
Figure 1B:
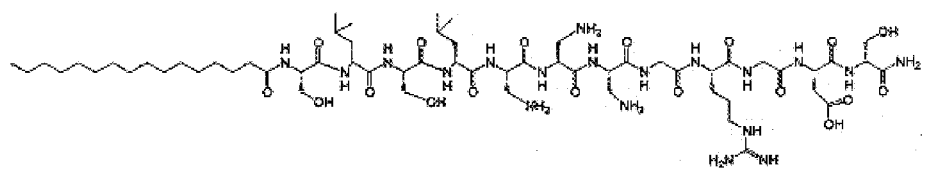
Figure 1C:
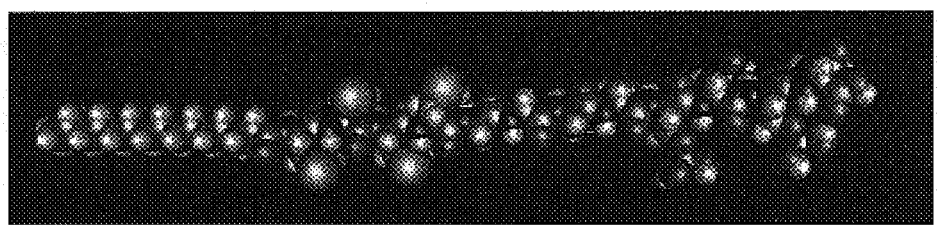
FIG. 1C illustrates a space filling model of the negatively charged peptide amphiphile of FIG. 1A.
Figure 2:
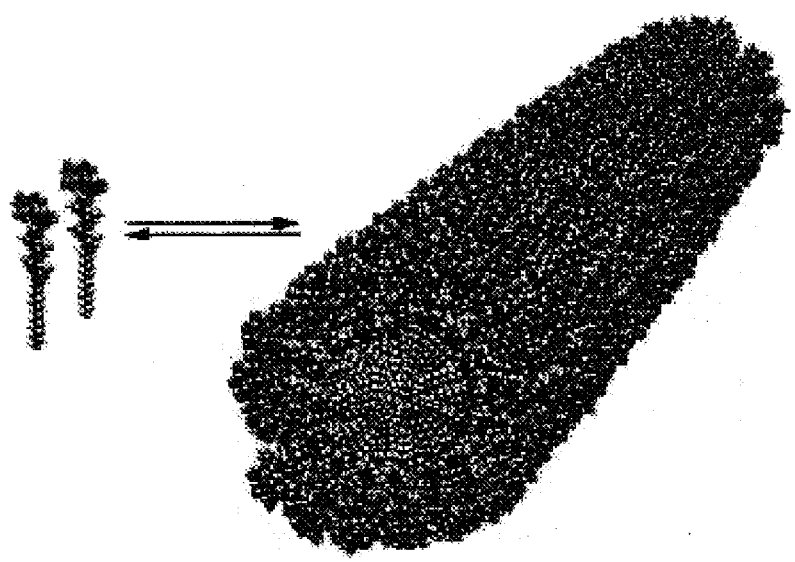
FIG. 2 is a space filling model illustrating the self assembly of peptide amphiphiles to form micelles like nanofibers according to the present invention.

The present invention includes the novel use of charged, and preferably highly negatively charged self-assembled peptide amphiphiles for biomineralization on a biologically compatible implant surface. Peptide amphiphile of the present invention are composed of three distinct segments as shown in FIG. 1A: a hydrophobic alkyl tail segment (A), a structural peptide segment which is flexible and may be hydrophobic (B), and a functional peptide segment (C) that includes charged groups and biological signals by virtue of the arrangement and choice of the amino acids in the segment. In an aqueous environment, such peptide amphiphile have the ability to self-assemble into cylindrical micelles also called nanofibers with the hydrophobic alkyl tails packed into the center and with the hydrophilic functional peptide head group exposed along the surface of the nanofiber as illustrated in FIG. 2. The functional head of the peptide anphiphile, PA, is bulky, giving the PA an overall conical shape. While not wishing to be bound by theory, it is thought that this shape as well as the hydrophobic and hydrophilic arrangement of the segments plays a critical role in PA self-assembly. With the functional peptide group exposed along the length of the fiber, a biological signal is presented to the environment. To enhance the robustness of the PA, the structural segment may contain four cysteine residues coupled to a triglycine spacer. When assembled into a fiber, the S-H ligands of neighboring cysteine residues are in close enough proximity to allow stable disulfide bond formation; exposure to oxidative conditions such as iodine or oxygen leads to disulfide bond formation and cross-linking of the fibers. One of the versatile features of the PA is its reversible cross-linking. The PA fibers can be disassembled using a reducing agent such as dithiolthreitol (DTT). The PA can also be self-assembled in a variety of ways, improving its adaptability for medical use.

FIG. 1 illustrates chemical connectivity of a peptide-amphiphile indicating three important segments for consideration in the design of the molecule: Segment A is a simple hydrophobic alkyl tail that can be a variety of sizes but must be greater than 6 carbon atoms in length. This portion of the peptide amphiphile serves to create the slender portion of the molecules conical shape. The alkyl tail is covalently bonded to the structural segment of the peptide amphiphile.

Segment B is a structural segment that covalently links the alkyl tail to the hydrophilic head group. The structural segment is covalently bonded at one end to the alkyl tail and at its other end is covalently bonded to the hydrophilic head group. If cross-linking is desired, cysteine amino acids may be utilized in this segment. If cross-linking is not desired, other amino acids such as but not limited to alanine, serine, or leucine may be used in this region (e.g. SLSL (SEQ ID NO:23) or AAAA (SEQ ID NO:24) as described in more detail herein). This cysteine-free system may be more appropriate for in situ biological applications where the environment may be more difficult to regulate. The SLSL (SEQ ID NO:23) modification to the system is expected to lead to a slower assembly of the nanofibers. Without wishing to be bound by theory, it is believed that the bulky leucine side chains may require more time to pack into the fiber. A slowed self-assembly may also have greater applications in a functional, in situ environment such as an operating room, where it may be advantageous to have delayed formation of the nano-fibers. The structural segment may also include a flexible linker composed of glycine or other amino acids. When the structural segment includes hydrophobic amino acids, it and the alkyl tail may be considered a hydrophobic segment. Where the structural segment includes hydrophilic amino acid, it and the hydrophilic head group may be considered as a hydrophilic segment.

Segment C includes the hydrophilic head group which is covalently bonded at one end to the structural segment and may be comprised of essentially any charged or hydrophilic amino acid such as serine, phosphorylated serine, diaminopropionic acid, diaminobutyric acid, and aspartic acid resulting in a highly charged peptide-amphiphile. Near physiological pH, these charged peptide-amphiphiles may be positively or negatively charged. The functional head of the peptide is a relatively bulky, charged segment of the molecule, and it serves as the widest region of the conical molecular geometry. The sequences listed in Table 1 represent various combinations of serine, phosphoserine, and aspartic acid (an amino acid sequences believed to be involved with calcium phosphates) and modified forms thereof. Though the actual configuration of the amino acids presented on the surface of the PA nanofibers has not yet been fully characterized, the different sequences described in Table 1 are intended to display different peptide moieties and charge concentrations on the outer surfaces of the assembled fibers. Self-assembly of PA mixtures may also allow for the presentation of different amino acid sequences along the length of an assembled fiber.

The peptide element of the PA is preferably carboxyl terminated, so that once assembled into fibers, these fibers may participate in further peptidic bonding, as to a functionalized metal surface, for example. The versatility and functionality of this self-assembling nanofibrous material may prove to be useful in mineralized tissue repair or reconstruction. It may also find application in regulation and inhibition of mineral formation. The potential for coating these compositions of the present invention on surfaces, such as titanium-based orthopedic implants, may furthermore enhance existing hard tissue engineering strategies.

The highly negatively charged peptide amphiphiles include charged amino acid sequences, such as serine, phosphorylated serine, and aspartic acid. Examples of such peptide amphiphiles include but are not limited to those in SEQ ID NO:1-21. A highly positively charged peptide amphiphile, SEQ ID NO:22, $C_{16}H_{31}O$-SLSLDprDprDprGRGDS may be used as a co-assembling peptide amphiphile to be mixed with useful negatively-charged molecules. This molecule, containing the GRGDS (residues 8-12 of SEQ ID NO:22) peptide sequence derived from adhesive proteins like fibronectin, would be expected to promote cell adhesion. This molecule is expected to have a (+3) charge at neutral pH. Higher positive charges for a peptide amphiphile could be obtained by increasing the number of 2,3-diaminopropionic acid, Dpr, units. Alternatively, the Dpr units could be replaced with residues including, but not limited to, lysine, arginine, or other positively-charged amino acids. Peptide components of the invention preferably include naturally occurring amino acids and artificial amino acids. Incorporation of artificial amino acids such as beta or gamma amino acids and those containing non-natural side chains, and/or other similar monomers such as hydroxyacids are also contemplated, with the effect that the corresponding component is peptide-like in this respect.

Various peptide amphiphile compositions and the highly charged peptide-amphiphiles in compositions of the present invention can be synthesized using preparatory techniques well-known to those skilled in the art, including those disclosed by Stupp et al WO 03/054146 A2 the contents of which are incorporated herein by reference in their entirety, and modifications of those originally described by Hartgerink, et al. (See e.g., J. D. Hartgerink, E. Beniash and S. I. Stupp, *Science* 294, 1683-1688, 2001), which is also incorporated in its entirety by reference. The synthetic schemes set forth in these references may be applied to the present invention. Peptide amphiphiles may be in their fully protonated form, partially protonated form, or as acid or basic addition salts. Generally such peptide amphiphiles can be made by standard solid-phase peptide chemistry including addition of an alkyl tail at the N-terminus of the peptide. Modifications of these synthetic methods can be made as would be known to those skilled in the art and aware thereof, using known procedures and synthetic techniques or straight-forward modifications thereof depending upon a desired amphiphile composition or peptide sequence.

Table 1 illustrates a number of highly charged peptide amphiphiles, having a net absolute charge greater than 3, actual charge ranging from +3 to −9, at substantially physiological pH, that may be similarly modified in accordance with the present invention The charge on these and other such peptide amphiphiles may be determined by titration or calculated from pK' as would be known to those skilled in the art.

TABLE 1

| SEQ ID NO | Alkyl tail (C = carbon, H = hydrogen) | Structural Peptide (N-terminus to C-terminus) | Functional Peptide (N to C) | Expected Charge (at pH 7) |
|---|---|---|---|---|
| SEQ ID NO 1. | $C_{16}H_{31}O$ | CCCCGGG | SS*DS*D | −7 |
| SEQ ID NO 2. | $C_{16}H_{31}O$ | AAAAGGG | SS*DS*D | −7 |
| SEQ ID NO 3. | $C_{16}H_{31}O$ | SLSLGGG | SS*DS*D | −7 |
| SEQ ID NO 4. | $C_{16}H_{31}O$ | CCCCGGG | S*S*DS*D | −9 |
| SEQ ID NO 5. | $C_{16}H_{31}O$ | AAAAGGG | S*S*DS*D | −9 |
| SEQ ID NO 6. | $C_{16}H_{31}O$ | SLSLGGG | S*S*DS*D | −9 |
| SEQ ID NO 7. | $C_{16}H_{31}O$ | CCCCGGG | DSS*DS* | −7 |
| SEQ ID NO 8. | $C_{16}H_{31}O$ | AAAAGGG | DSS*DS* | −7 |
| SEQ ID NO 9. | $C_{16}H_{31}O$ | SLSLGGG | DSS*DS* | −7 |
| SEQ ID NO 10. | $C_{16}H_{31}O$ | CCCCGGG | DS*S*DS* | −9 |
| SEQ ID NO 11. | $C_{16}H_{31}O$ | AAAAGGG | DS*S*DS* | −9 |
| SEQ ID NO 12. | $C_{16}H_{31}O$ | SLSLGGG | DS*S*DS* | −9 |
| SEQ ID NO 13. | $C_{16}H_{31}O$ | CCCCGGG | SDS*DS* | −7 |
| SEQ ID NO 14. | $C_{16}H_{31}O$ | AAAAGGG | SDS*DS* | −7 |
| SEQ ID NO 15. | $C_{16}H_{31}O$ | SLSLGGG | SDS*DS* | −7 |
| SEQ ID NO 16. | $C_{16}H_{31}O$ | CCCCGGG | S*DS*DS* | −9 |
| SEQ ID NO 17. | $C_{16}H_{31}O$ | AAAAGGG | S*DS*DS* | −9 |
| SEQ ID NO 18. | $C_{16}H_{31}O$ | SLSLGGG | S*DS*DS* | −9 |
| SEQ ID NO 19. | $C_{16}H_{31}O$ | CCCCGGG | DS*DS*D | −7 |
| SEQ ID NO 20. | $C_{16}H_{31}O$ | AAAAGGG | DS*DS*D | −7 |
| SEQ ID NO 21. | $C_{16}H_{31}O$ | SLSLGGG | DS*DS*D | −7 |
| SEQ ID NO 22 | $C_{16}H_{31}O$ | SLSLDprDprDpr | GRGDS | +3 |

Peptide symbol legend: A = alanine; C = cysteine; G = glycine; L = leucine; S = serine; and S* = phosphorylated serine (also referred to as S(P)); Dpr—2,3–diaminopropionic acid.

The peptide amphiphile, SEQ ID No:1, shown in FIG. 1A, contains the highly charged peptide sequence SS(P)DS(P)D (residues 8-12 of SEQ ID NO:1), a sequence specifically chosen to model the protein phosphophoryn (FIG. 1A). Phosphophoryn is found in dentin and contains large numbers of aspartic acid and phosphoserine residues in repeat sequences of [SDS] and [DSS]. The [SDS] repeat gives phosphoserines paired along the same edge of the extended chain, with a negatively charged aspartic acid residue in between. Phosphophoryn plays a role in the biomineralization process where it is thought to both nucleate and inhibit crystal growth depending on the reaction conditions. The negative charge of repeating [SD] is thought to have a strong calcium binding potential and lead to a local concentration of ions. Emulation of the [SDS] motif in the design of the PA gives the PA an overall −7 charge for its functional peptide head.

The formation of a self-supporting matrix or solid nanofiber comprised of negatively charged peptide amphiphiles under physiological conditions affords the opportunity to utilize this material for a wide range of purposes, e.g., mineralized tissue repair or reconstruction, regulation and inhibition of mineral formation, and coating orthopedic implants or the like. The amino acid sequences present in the functional elements of the peptides are believed to be particularly suitable for mineralization in vertebrate tissue environments. The amino acid sequences particularly useful for mineralization may be selected also impart a negative charge to peptide amphiphiles and or self assembled nanofibers thereof in aqueous solution under physiological conditions. For negatively charged peptide amphiphiles the charge is preferably −4 or more negative, even more preferably in the range of −5 to −7, and most preferably −7 or more negative. This charge may allow orientation of assembled fibers both in bulk and once assembled on substrates.

While not wishing to be bound by theory, it appears that specific negatively charged, or phosphorylated amino acids, play an important role in the molecular interactions with growing crystals or biological materials like bone and dentin. It appears that the negative charges in these peptide sequences may interact strongly with positive $Ca^{+2}$ ions. It also appears that the negative phosphate on a phosphoryllated serine may be incorporated into a crystal, serving either as a nucleator or an inhibitor. For example, it is believed that phosphorylated forms of the [DS*S*] repeat are suspected to be the critical sequences for mineral interaction. The presence of a S(P) in a peptide amphiphile leads to directed, apatitic mineralization of assembled PA nanofibers. The PAs of the present invention have been designed with the intention of enhancing the influence of the PA nanofibers on mineral regulation. The present invention provides for a series of peptide amphiphiles having a large negative charge and peptide sequences mimicking natural sequences found in phosphophoryn. depending upon the choice of amino acids, the peptide amphiphile presents signals capable of stimulating cell adhesion or mineralization at the site.

Self-assembly generally occurs at predetermined concentrations of the peptide amphiphile to form self-supporting gel. To induce self-assembly of the highly charged peptide-amphiphile, the pH of the solution may be lowered or raised, ions may be added to the solution, and the solution may be subject to dehydration or drying. Peptide amphiphiles may be in their fully protonated form, partially protonated form, or as acid or basic addition salts. The addition of polyvalent metal ions may induce gel formation of the negatively charged peptide-amphiphiles at physiological conditions. A number of negatively charged peptide-amphiphiles self-assembled into nanofibers by addition of polyvalent $Ca^{+2}$, $Mg^{+2}$, $Zn^{+2}$, $Cd^{+2}$, $Fe^{+2}$, $Gd^{+3}$. Peptide amphiphiles may also be self assembled by addition of oppositely charged peptide amphiphiles. A non-limiting example of such co-assembly to form nanofibers may include combining 3 equivalents of $C_{16}H_{31}$O-SLSLD-prDprDprGRGDS, SEQ ID NO:22, with $C_{16}H_{31}$O-CCCCGGGSS*DS*D, SEQ ID NO: 1. The resulting coassembly forms a self-supporting PA nanofiber gel. Similar approaches may be applied using variations the charged molecules involved. Lowering the pH induces self assembly of solubilized negatively charged peptide amphiphiles while raising the pH may be used to induce self assembly of solubilized positively charged peptide amphiphiles.

According to existing knowledge of amphiphile self-assembly, an alkyl tail with about 6-16 carbon atoms coupled to an ionic peptide should create an amphiphile that assembles in water into cylindrical micelles because of the amphiphiles overall conical shape. Preferably the alkyl tail has 6 or more carbon atoms. The alkyl tails pack in the center of the micelle with the peptide segments exposed to an aqueous environment as shown schematically in FIG. 2. These cylindrical micelles can be viewed as fibers in which the chemistry of the peptide region is repetitively displayed on their surface. Similar amphiphile molecules can also be designed to provide micelles having structural shapes that may differ from a fiber like appearance such as but not limited to spheres. Other compositions may also be used to induce predetermined geometric orientations of the self-assembled amphiphile peptides.

Figure 3:
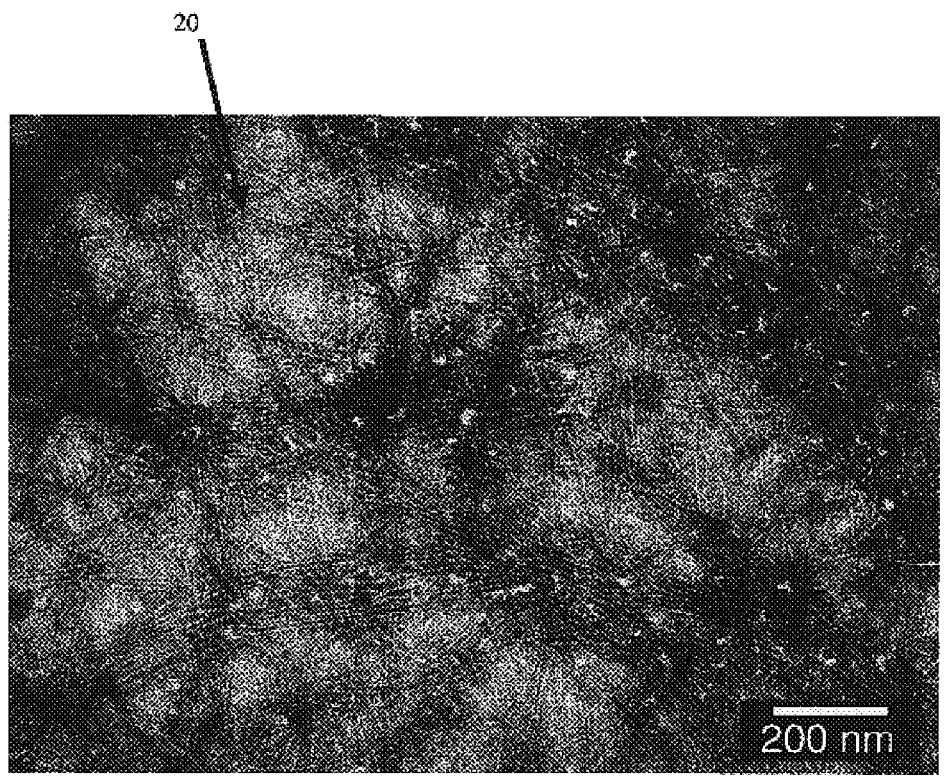
FIG. 3 illustrates a TEM micrograph of the peptide-amphiphile nanofibers 20formned by a decrease in pH of a peptide amphiphile composition SEQ ID NO:1, $C_{16}H_{31}O$-CCCCGGGSS(P)DS(P)D.

According to the present invention, negatively charged peptide amphiphile molecules can be self-assembled from aqueous solutions to form relatively clear, colorless, self-supporting gels by various agents including but not limited to: lowering of solution pH to make it acidic, such as below approximately pH 4, addition of divalent ions, such as $Ca^{+2}$, and dehydration (drying). For positively charged peptide amphiphiles, self assembly may be induced by agents including but not limited to raising the solution pH and making it basic generally above about pH 8, or by adding negatively charged ions including negatively charged peptide amphiphile to induce coassembly, and dehydration. Other method of self assembly useful in the present invention are disclosed in U.S. Provisional Pat. Application Ser. No. 60/245,689, filed Nov. 12, 2002, the contents of which are incorporated herein by reference in their entirety. Whether a particular agent is suitable for initiating self assembly of the charged peptides may be determined by transmission electron microscopy (TEM) of agent treated solutions. For example, TEM reveals that negatively charged peptide amphiphiles are induced to form gels by a change in pH. These gels, as shown in FIG. 3, are composed largely of nanofibers approximately 5-10 nm in diameter of self assembled peptide amphiphiles. Although the invention is described in detail with respect to peptide amphiphiles in aqueous solution, the presence of non-aqueous liquids in the solution in part or in whole, such as but not limited to ethanol, will not limit the scope of the invention.

At neutral pH, the negatively charged peptide amphiphiles alone do not self-assemble because of the strong electrostatic repulsion of the like charged peptide head groups. When the pH is lowered with the addition of HCl, the negative charges are eliminated allowing the hydrophobic alkyl tails to pack together. At neutral pH, the PAs can be self-assembled with the addition of divalent ions such as $Ca^{2+}$, which is thought to shield the negative charge of the head groups. Simply drying the PA on a surface also leads to the formation of nanofibers. Without wishing to be bound by theory, increased concentration due to drying is believed to play a role in self assembly of the peptide amphiphiles. The present invention is directed to various modes of self-assembly and controlled self-assembly of highly charged peptide-amphiphiles. More particularly, preferred embodiments of the present invention are directed to a highly charged self-assembled peptide-amphiphile nanofiber network at physiological conditions. For purposes of this invention physiological conditions can include temperature, pH, as well as ions and their concentration present in blood plasma and other bodily fluids.

Figure 6A:
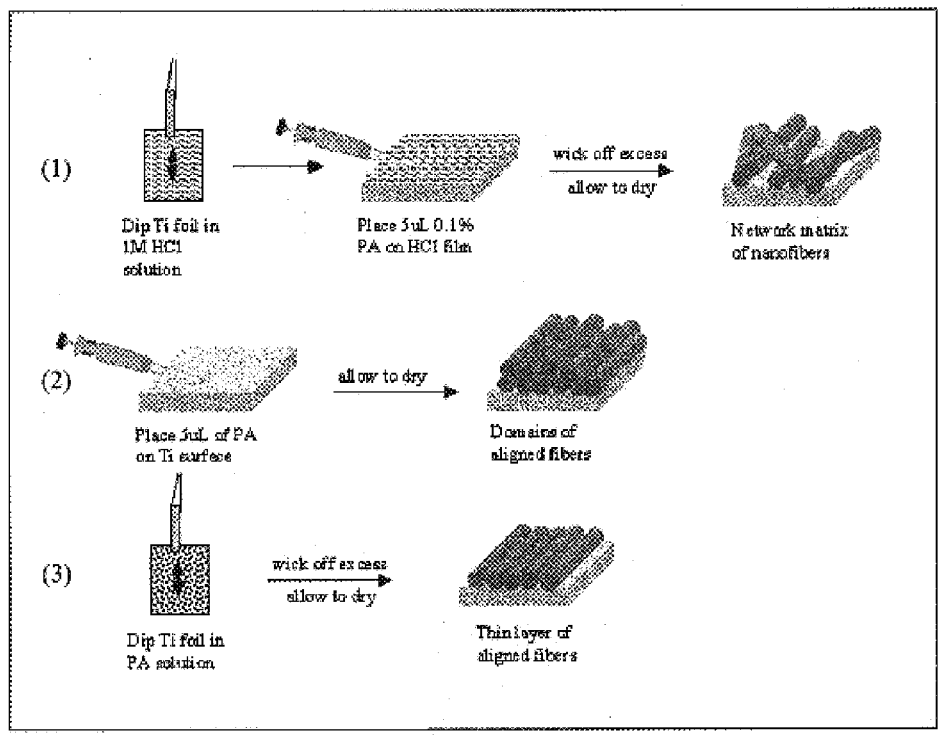
FIG. 6A illustrates schematically several methods for arranging self assembled peptide amphiphile nanofibers on a substrate.
Figure 6B:
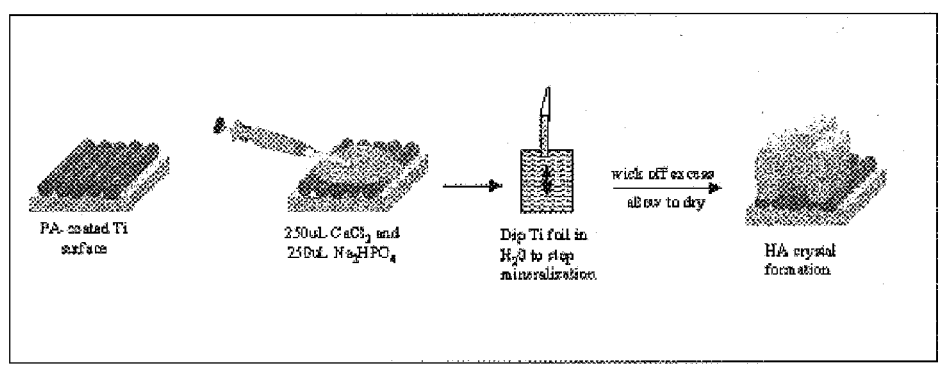
FIG. 6B illustrates a method for orienting hydroxyapatite crystals on oriented self assembled peptide amphiphiles on a substrate.

The orientation of self assembled nanofibers on a biologically compatible implant surface coated with such nanofibers may be controlled by various treatments. One such treatment achieves alignment of PA fibers on the biologically compatible implant surface through different drying techniques. As illustrated in FIG. 6A(1), a network of randomly oriented fibers may be formed on a substrate by dipping the substrate in a medium, such as HCl or divalent ions which causes self assembly, adding peptide amphiphile to the surface of the substrate and allowing the excess to wick off and then allowing this surface mixture to dry. As illustrated in FIG. 6A(2) domains of aligned fibers may be formed on a substrate by placing peptide amphiphile directly on the surcae and allowing it to dry. Alternately, as illustrated in FIG. 6A(3), a thin layer of aligned fibers may be formed by immersion of the substrate in a solution of the peptide amphiphile, the excess PA solution allowed to wick off, and then allowing the remaining peptide amphiphile to dry and self assemble. By changing the relative concentrations of the PA and the mineralization conditions, nucleation and inhibition of HA minerals on self assembled peptide amphiphiles is achieved. Preferential alignment of mineral or biological materials may be achieved with aligned self assembled peptide nanofibers as illustrated in FIG. 6B.

Where the self assembled peptide amphiphiles are coated onto a substrate, the substrate to be coated is preferably a biologically compatible material and may include polymers, metals, metal alloys, ceramics or a combination of these. The substrate preferably has the shape for its intended use prior to coating. Implant examples may include hip and knee implants, plates and pins for broken bones, dental implants, and other reconstructions. Substrates useful in the practice of this invention may have an oxide surface, a hydroxide surface, or combination of these groups coating at least a portion of the surface of the substrate. Metals and alloys useful in the practice of this invention may include but are not limited to titanium and alloys thereof, surgical steels, amalgams, Co—Cr alloys, tantalum, or silicon materials. Preferably the substrate is an alloy of titanium alloy, an example of which is a titanium alloy called Ti-6A1-4V which is useful for orthopedic and dental implants. The metal or alloy may be a bulk material, a porous foam, or a coating or a deposited as an adherent film on another substrate like a ceramic. Suitable ceramic materials present oxide and hydroxide functionalities, for example alumina, sapphire, and calcium phosphate ceramics such as sintered apatite.

Biocompatible, biodegradable, gels are useful as a means of delivering templates, which may or may not include isolated cells, into a patient to create an organ equivalent or tissue such as cartilage. The gels promote engraftment and provide three-dimensional templates for new growth. The resulting tissue is generally similar in composition and histology to naturally occurring tissue. Compositions which include a self-assembling peptide-amphiphile solution may be directly injected into a site in a patient, where the self-assembled peptide amphiphile gel organizes into a matrix. Alternatively, cells are suspended in a self-assembled peptide amphiphile gel that is poured or injected into a mold having a desired anatomical shape, then organize to form a matrix which can be implanted into a patient. Ultimately, the self-assembled peptide amphiphile gel degrades, leaving only the resulting tissue. The peptide amphiphiles of the present invention may be used in conjunction with other tissue engineering material, either as a gel, solid, or liquid and are used to template tissue growth in a pre-determined area.

Self-assembly and/or gelation under physiological conditions makes available a system for the formation of micellular nanofibers in an aqueous environment at neutral and/or physiological pH conditions. Such a combination can be used to assemble nanofibers with a range of residues providing a variety of chemical or biological signals for corresponding cell adhesion, yielding enhanced properties with respect to tissue engineering or regenerative applications. It is contemplated that, alone or in conjunction with the other factors discussed herein, that preferred medical or therapeutic embodiments of such a system can be utilized.

The chemical and/or biological stability of the nanofibrous system may be used to control the rate of degradation, therapeutic delivery or release of cells, or release of other beneficial agents using the nanofibers as the carriers. The concentration and degree of cross linking of cysteine residues in the self assembled charged peptide amphiphiles can be varied to control this reactivity or stability. Furthermore, enzymes could be incorporated in the nanofibers to control biodegradation rate through hydrolysis or reduction of the disulfide bonds. Such degradation and/or the concentration of the cysteine residues can be utilized in a variety of tissue engineering contexts. The thiol moieties of cysteine residues can be used for intermolecular disulfide bond formation through introduction of a suitable oxidizing agent or under physiological conditions. Conversely such bonds can be cleaved by a reducing agent introduced into the system or under reducing conditions.

As a self-supporting nanofiber gel, the self assembled charged peptide amphiphiles may be used as a mineralizable bone-defect filler. The self assembly of the peptide amphiphiles in the presence of biological ions such as $Ca^{+2}$ may make the material particularly valuable for in situ gel formation. It may also be used as a biological coating for orthopedic implants. These applications could find particularly valuable use in addressing medical problems such as osteooncology, congenital bone and tooth defects, osteoporosis, synthetic teeth, and dental implants. The strong binding affinity of the negative peptide amphiphile is also expected to have potential as a mineral inhibitor, in which case, it could be used in applications related to vascular calcification or even in the treatment of other unwanted calcifications, such as kidney stone formation.

The mineralization potential of the peptide amphiphile couples with the biocompatibility of titanium implant surfaces to create a complete system for hard tissue engineering. Mineralized PA fibers could be naturally degraded during the bone remodeling process. The organization of the PA fibers on the titanium surface could be directly controlled through different drying procedures, one of which results in large regions of aligned fibers. Hydroxyapatite nanocrystals formed in a $Ca^{2+}$ induced self assembled bulk peptide amphiphile gels show preferential alignment, suggesting an intimate association with the fibers, while a PA coated Ti surface discourages HA crystal formation. Just as phosphophoryn has been shown to both nucleate and inhibit HA crystal formation, it is possible that the highly charged PA may be found to have a versatile role that mimics nature.

Various aspects of the present invention will be illustrated with reference to the following non-limiting examples.

EXAMPLE 1

This example describes the synthesis of the peptide amphiphile SEQ ID NO:1, $C_{16}H_{31}$O-CCCCGGGSS(P)DS(P)D).

Solvents and reagents for peptide synthesis were purchased from Fisher Scientific and Sigma-Aldrich respectively, while amino acids and resins were provided by Novabiochem (San Diego, Calif.) and Applied Biosystems (Foster City, Calif.).

The synthesis of the peptide portion of the molecule was performed using standard solid phase synthesis on an Applied Biosystems 433A automated peptide synthesizer. The peptide was grown on an aspartic acid-functionalized Wang polystyrene resin, using Fmoc protection of the amine terminus. 0.95 molar equivalents of HBTU and 6 equivalents of diisopropylethylamine (DEEA) were used for each new amino acid coupled to the resin. A sixteen-carbon alkyl tail was subsequently added to the N-terminus of the peptide manually, by adding 3 molar equivalents of palmitic acid to the peptide, in the presence of 0.95 palmitic acid molar equivalents HBTU and 12 peptide molar equivalents of DIEA. The peptide amphiphile was then cleaved from the polystyrene resin and amino acid side groups were deprotected in 95% trifluoroacetic acid (TFA), 2.5% triisopropylsilane (TIS), 2.5% deionized water. TFA was removed in a rotary evaporator and the peptide was collected by precipitation in cold diethyl ether. Filtered product was dried and frozen for storage. Once synthesized, the molecules were dissolved at 10 mg/mL in slightly basic water (pH=7.5-8) and distributed in 1 mL aliquots. These aliquots were lyophilized and stored at −30° C. Electrospray ionization mass spectrometry performed on dilute solutions is used to confirm the peptide sequence.

This PA may be self-assembled under acidic conditions below pH 4, by addition of cations, such as $Ca^{2+}$, by coassembly with other charged molecules such a positively charged peptide amphiphiles or by drying.

EXAMPLE 2

This example illustrates the self assembly of negatively charged peptide amphiphiles using positively charged peptide amphiphiles, coassembly, to induce nanofiber gel formation. An aliquot of 50 mL of 10 mg/mL SSDSD PA, SEQ ID NO:25, was mixed with 150 mL, approximately 3 molar equivalents, of $C_{16}H_{31}O$-SLSLDprDprDprGRGDS, SEQ ID NO:22.The resulting coassembly forms a self-supporting PA nanofiber gel. Similar approaches may be applied using variations the charged molecules involved.

EXAMPLE 3

This example illustrates the synthesis of a positively charged peptide amphiphile SEQ ID NO:22, $C_{16}H_{31}O$-SLSLDprDprDprGRGDS having a +3 charge.

Solvents and reagents for peptide synthesis were purchased from Fisher Scientific and Sigma-Aldrich respectively, while amino acids and resins were provided by Novabiochem (San Diego, Calif.) and Applied Biosystems (Foster City, Calif.).

The synthesis of the peptide portion of the molecule wass performed using standard solid phase synthesis on an Applied Biosystems 433A automated peptide synthesizer. The peptide is grown on a Rink amide MBHA polystyrene resin, using Fmoc protection of the amine terminus. 0.95 molar equivalents of HBTU and 6 equivalents of diisopropylethylamine (DIEA) were used for each new amino acid coupled to the resin. A sixteen-carbon alkyl tail was subsequently added to the N-terminus of the peptide manually, by adding 3 molar equivalents of palmitic acid to the peptide, in the presence of 0.95 palmitic acid molar equivalents HBTU and 12 peptide molar equivalents of DIEA. The peptide amphiphile was then cleaved from the polystyrene resin and amino acid side groups are deprotected in 95% trifluoroacetic acid (TFA), 2.5% triisopropylsilane (TIS), 2.5% deionized water. TFA is removed in a rotary evaporator and the peptide is collected by precipitation in cold diethyl ether. Filtered product is dried and frozen for storage. Once synthesized, the molecules are dissolved at 10 mg/mL in water at neutral pH and distributed in 1 mL aliquots. These aliquots are lyophilized and stored at −30° C. Electrospray ionization mass spectrometry performed on dilute solutions is used to confirm the peptide sequence.

The charged peptide amphiphile SEQ ID NO:22, $C_{16}H_{31}O$-SLSLDprDprDprGRGDS may be self-assembled under basic conditions (pH >8), by drying onto a surface, or by coassembly with other charged molecules, such as a negatively-charged vide supra.

EXAMPLE 4

This example illustrates the growth and differentiation of cells on self assembled peptide nanofibers coated on a substrate.

Cell culture preparation includes treating glass coverslips overnight in 100% ethanol. 25 mL of SEQ ID NO:1, was spin-coated at 1500 r.p.m. for 30 seconds onto the treated glass cover slips. Samples were dried under vacuum to promote self-assembly on the glass surface. Samples were then immersed in 10% iodine for 15 minutes to cross-link the assembled PA nanofibers. Cross-linked samples were thoroughly, but gently rinsed by immersion in water 3×. Rinsed slides were dried by vacuum desiccation and placed in a 24-well tissue culture well plate. MC3T3-E1 mouse calvarial osteoblasts were plated at 10,000 cells/coverslip in 1 mL of MEM-a culture medium containing 10% fetal bovine serum, 1% penicillin/streptomycin, 30 mM β-glycerolphosphate, and 50 mg/mL ascorbic acid. The medium was exchanged every 3 days.

Figure 4A:
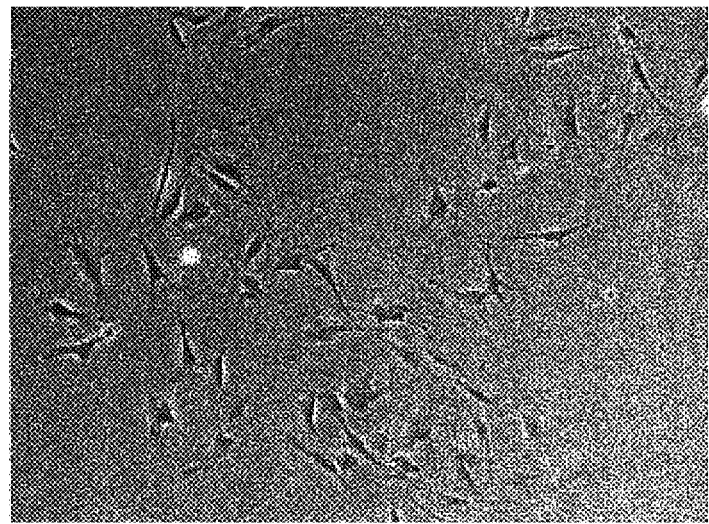
FIG. 4A is an optical phase contrast micrograph of mouse calvaria MC3T3-E1 osteoblastic cells on self assembled peptide amphiphile, SEQ ID NO 1 coated on glass after 24 hours.
Figure 4B:
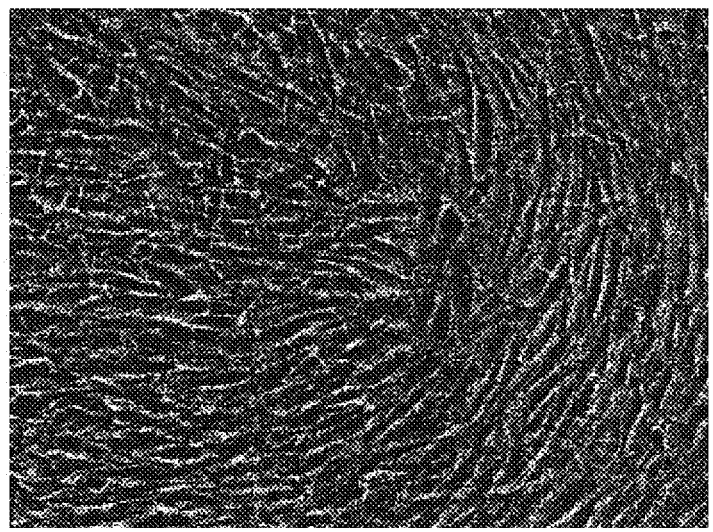
FIG. 4B is an optical phase contrast micrograph of a confluent layer of mouse calvaria MC3T3-E1 osteoblastic cells on self assembled peptide amphiphile, SEQ ID NO 1, coated on glass after 12 days; the cell spreading and proliferation illustrated in the micrographs demonstrate the biocompatibility of peptide amphiphile nanofibers for bone tissue engineering.
Figure 5:
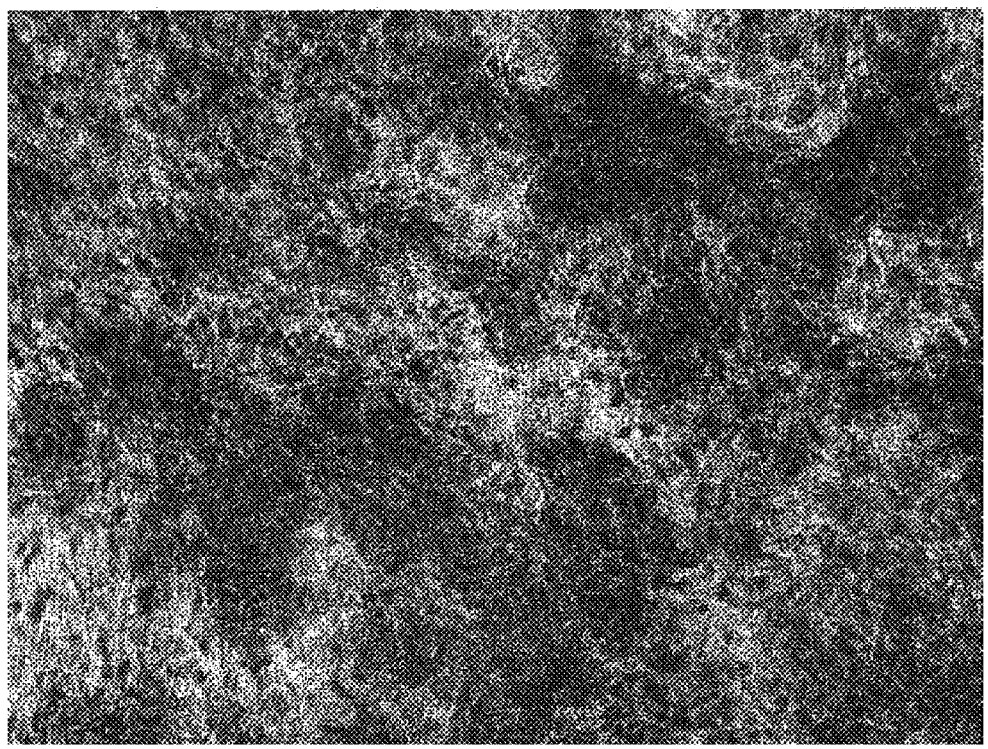
FIG. 5 is an optical micrograph of mouse calvaria MC3T3-E1 osteoblastic cells on self assembled peptide amphiphile, SEQ ID NO 1 coated on glass after 17 days with Von Kossa staining; mineral formation is evidenced by dark patterns on stained cell layer.

Cells were seen adhering and spreading on the nanofiber-coated glass slides, proliferating over 12 hours, FIG. 4A, to form a confluent cell layer after 24 hours FIG. 4B. By 17 days of culture, the cells showed signs of osteoblastic diffentiation, producing significant mineral, evidenced by Von Kossa staining as shown in FIG. 5. These experiments demonstrate the biocompatibility of these nanofibers.

EXAMPLE 5

This example illustrates the strong affinity of the nanofibers formed from charged self assembled peptide amphiphiles for calcium phosphate constituents. The affinity is demonstrated by mineralization of charged peptide amphiphiles that have been coated and self assembled onto a surface as well as mineralization of charged peptide amphiphiles which have self assembled to form a bulk gel.

Synthesis of peptide amphiphile, SEQ ID NO:1, was synthesized with standard Fmoc chemistry on an Applied Biosystems 733A automated peptide synthesizer. The peptide was grown from the C terminus to N terminus with the sequence CCCCGGGSS(P)DS(P)D, SEQ ID NO:1, and the N terminus was capped with a 16 carbon fatty acid. The synthesis of the peptide amphiphile, SED ID NO:1, was verified by ESI mass spectroscopy indicating correct molecular weight. HPLC of the molecule showed a single pure product. 1% and 0.1% solutions of SEQ ID NO:1 were found to gel by HCl and $Ca^{2+}$ addition. To confirm the formation of fibers, transmission electron microscopy (TEM) images of these bulk gels were taken and are shown in FIG. 3. Fibers on the order of 5-10 nm in diameter can be seen, as well as globular micelles ranging from 10-15 nm in diameter.

Figure 7:
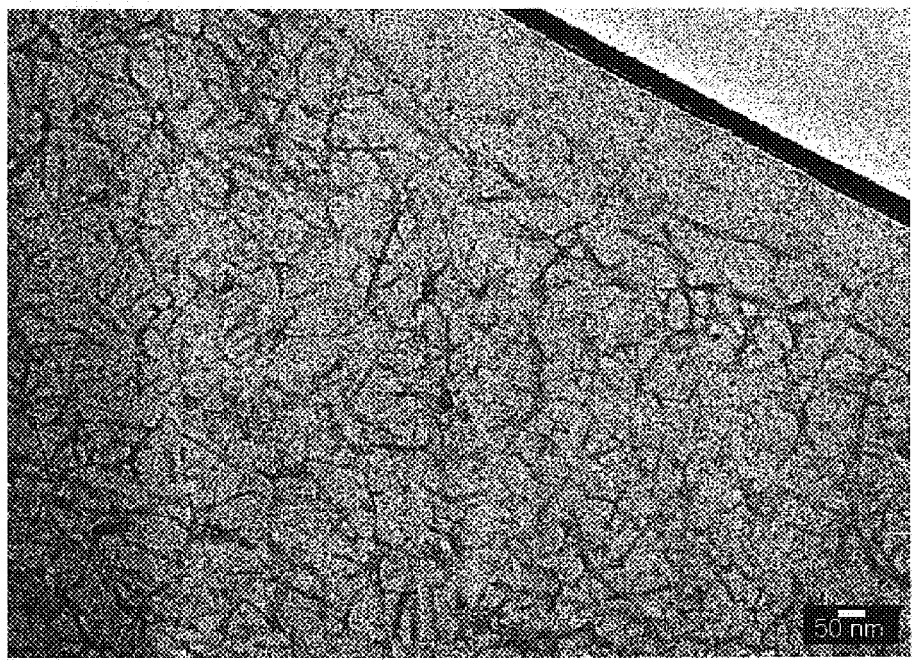
FIG. 7 is a transmission electron micrograph of peptide amphiphiles, SEQ ID NO:1, dried directly on a TEM grid, stained, and illustrating an amorphous mineral deposit by the dark patterns on the stained layer.

Mineralization of charged peptide amphiphiles deposited on holey, carbon coated copper TEM grid surfaces involved drying a drop of PA, SEQ ID NO:1, dried directly on the grid and treating with $CaCl_2$ (5 mM) on one side and $Na_2HPO_4$ (3 mM) on the other side of the grid in a 5:3 molar ratio, respectively. In this manner, the solutions mixed only via diffusion through the holes in the carbon support and the peptide amphiphile, SEQ ID NO:1, film. Samples were allowed to react in a humidified atmosphere at 37° C. Mineralization experiments lasted from 30 min to overnight, with the mineralization terminated by dipping the grid surface repeatedly in water. Mineral stained fibers are clearly seen on the grid surface, with the surface of the fibers covered in an amorphous mineral deposit as shown in FIG. 7. The relatively high contrast of these otherwise unstained fibers suggests that they are encased in an amorphous mineral deposit. Though the organization of calcium and/or phosphate on the fibers is unclear, the observed staining suggests a strong affinity of the fibers for calcium phosphate constituents.

Figure 8:
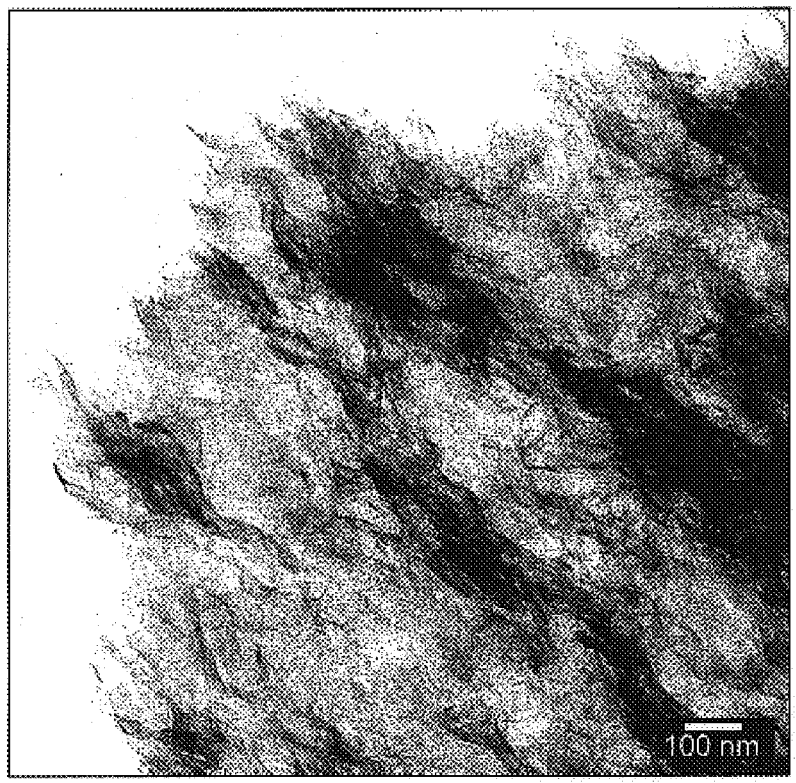
FIG. 8A is a transmission electron micrograph of calcium phosphate nanocrystals, dark regions, within a gel of self assembled charged peptide amphiphiles, SEQ ID NO:1.
FIG. 8B illustrates diffraction rings of the calcium phosphate nanocrystals within the gel. Arcing in the (002) diffraction ring indicate alignment of the nanocrystals along their c-axes.
Figure 8B:
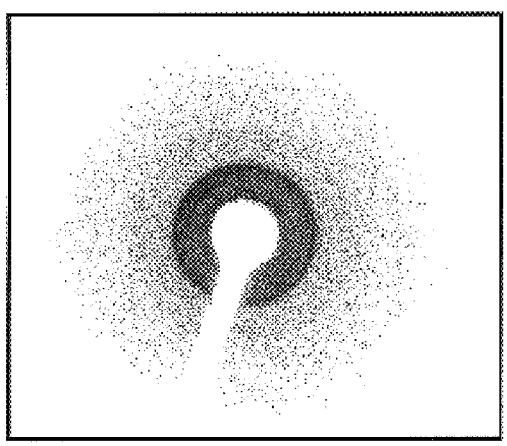

Mineralization of bulk PA gels, SEQ ID NO:1, consisted of dissolving $Na_2HPO_4$ (1.2 mM) in 1 mL of 0.05% aqueous peptide amphiphile, SEQ ID NO:1. To this, 20 µL of 0.25M $CaCl_2$ was added. Here, the $Ca^{2+}$ served first to induce gelation and subsequently to participate in mineralization. The mineralization of a bulk cel SEQ ID NO:1, was analyzed by TEM. The gel was created by adding phosphate to an aqueous peptide amphiphile solution, SEQ ID NO:1, and then adding $Ca^{2+}$ to both induce assembly and participate in mineralization. The TEM reveals the formation of nanocrystals of calcium phosphate, consistent in size and morphology with those found in natural tissue as shown in FIG. 8A. Furthermore, the diffraction rings of this material shown in FIG. 8B, correspond consistently with d-spacings for hydroxyapatite. These crystals are preferentially aligned along their c-axes as indicated by the arcs in the (002) ring seen in the corresponding electron diffraction pattern. Although the fibers are unable to be resolved, the consistent and persistent orientation of the crystals suggests that the fibers may play a role in aligning these crystals. Such an influence is quite similar to the influence of collagen on HA crystals in natural bone.

EXAMPLE 6

This example shows how self assembled charged peptide amphiphile nanofiber orientation on a substrate surface may be controlled by different drying procedures.

Methodology for titanium surface preparation. Titanium-6A1-4V foils were cut into 5 mm by 5 mm squares and pretreated to remove contaminants by ultrasonically washing for 15 min each with methylene chloride, acetone, and water. The samples were then etched in 0.25% HF, 2.5% $HNO_3$ at room temperature for 1 min, followed by passivation in 40% $HNO_3$ for 30 min. Samples were washed extensively with water and stored until later use. The above etching concentration and time were found to give the cleanest Ti surface.

Peptide amphiphile coating of titanium foil surfaces was performed by different methods. Various concentrations of PA solution were dried on the Ti foils in three ways as illustrated in FIG. 6A. In FIG. 6A (1), the foils were dipped in 1M HCl; aqueous PA was then added on top of the HCl film and allowed to dry. In FIG. 6A (2), a single drop of aqueous PA was placed on the foils and allowed to dry. Lastly, in FIG. 6A (3), the foils were dipped into a solution of PA, the excess PA wicked off, and then dried in air.

Figure 9A:
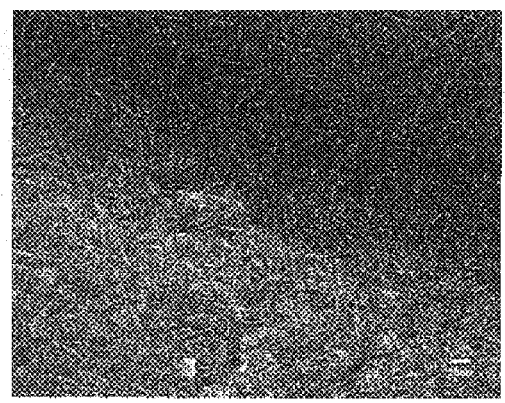
FIG. 9A is an SEM of peptide amphiphiles, SEQ ID NO:1, dried on top of an aqueous HCl film to self assemble the peptide amphiphiles on a titanium substrate (method (1) from FIG. 6A)
Figure 9B:
FIG. 9B is an SEM of peptide amphiphiles, SEQ ID NO:1 self assembled directly on top of a titanium surface by drying (method (2) from FIG. 6A)
Figure 9C:
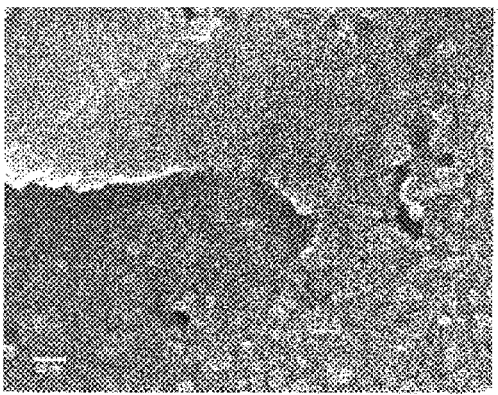
FIG. 9C is an SEM of peptide amphiphiles, SEQ ID NO:1, self assembled on a titanium substrate after dipping and wick drying (method (3) from FIG. 6A)

Using a titanium substrate, when an aqueous solution of a peptide amphiphile SEQ ID NO:1 was dried on top of an HCl film as illustrated by the method in FIG. 6A (1), a network matrix of fibers was observed to form using SEM as shown in FIG. 9A. While not wishing to be bound by theory, it is believed that fibers formed under pH induced assembly in the thin acid film, and that these preformed fibers dried onto the Ti surface. In contrast, when a single drop of aqueous PA was placed on the Ti surface, as illustrated by the method in FIG. 6A (2), a rather thick coating of PA was observed to form using SEM as shown in FIG. 9B. Domains of aligned fibers were seen on the surface of large flat plates of dried peptide amphiphile SEQ ID NO:1. The underlying layers could not be characterized and their organization is unknown. Large regions of aligned fibers were observed as shown in FIG. 9C, when a Ti foil was dipped in peptide amphiphile, SEQ ID NO:1, solution and then wick-dried, as illustrated by the method in FIG. 6A (3). The wicking procedure resulted in a very thin layer of self assembled charged peptide amphiphile SEQ ID NO:1 on the Ti sample, which is thought to have played a role in the greater alignment of fibers. While it is uncertain whether the wick-drying procedure results in a monolayer of fibers, the layer of PA fibers was very thin as evident from the ability to discern features of the Ti surface that were not seen with either of the two other preparations.

EXAMPLE 7

This example illustrates that charged self assembled peptide amphiphiles of the present invention coated onto a surface may be used to control the extent of hydroxyapatite growth on the peptide amphiphile coated surface.

Figure 10A:
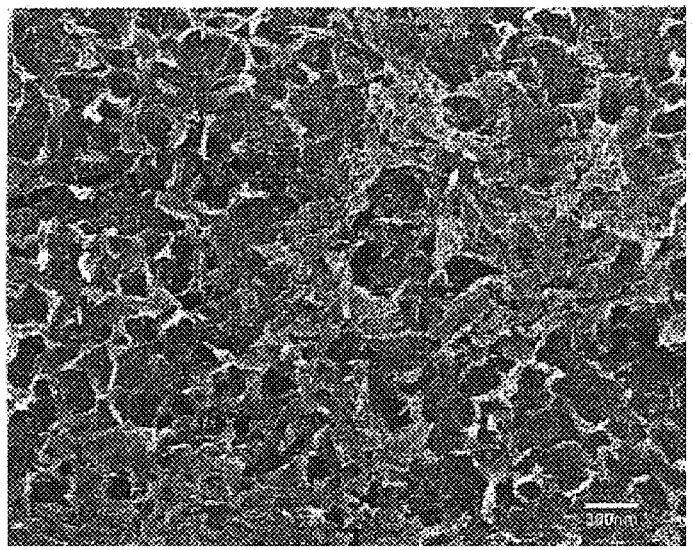
FIG. 10A is a bare titanium surface after 24 hours mineralization treatment.
Figure 10B:
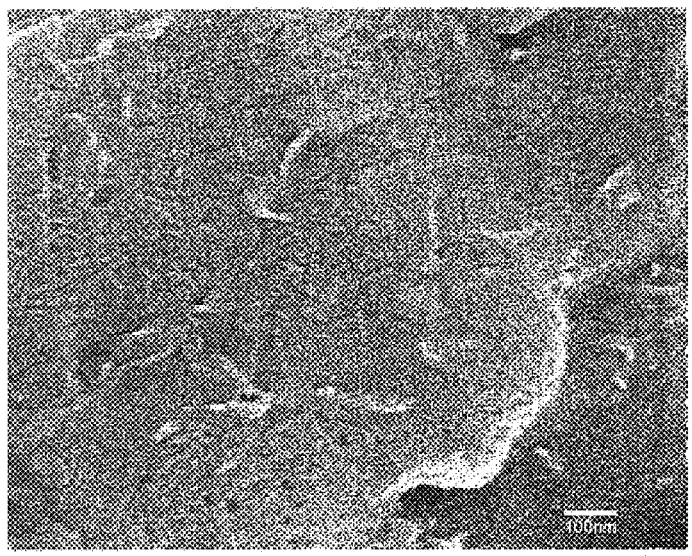
FIG. 10B is a titanium surface, coated with self assembled charged peptide amphiphile, SEQ ID NO:1, after 24 hours mineralization treatment.

Peptide amphiphile coated Ti surfaces were mineralized by treatment in 2 mM $CaCl_2$ and 1.2 mM $Na_2HPO_4$. Mineralization experiments lasted from 30 min to overnight, with the mineralization terminated by dipping the foils repeatedly in water. Results of mineralization experiments of a titanium foil and a titanium foil coated with the charged peptide amphiphile, SEQ ID NO:1, are shown in FIG. 10A and in FIG. 10B respectively. Titanium foil was coated with peptide amphiphile solution, SEQ ID NO:1, which was allowed to self assemble by evaporation. This nanofiber coated titanium foil was subsequently coated with calcium phosphate by the method illustrated in FIG. 6B. The SEM in FIG. 10B show that the self assembled charged peptide amphiphile nanofibers on the surface of the titanium foil control the formation of hydroxyapatite crystals on the titanium foil surface. In both 1 hr and 24 hr mineralizations, fewer hydroxyapatite crystals were observed on the self assembled peptide amphiphile coated titanium foil samples compared to mineralized titanium foil controls FIG. 10A. The number of crystals found on the surface of the peptide amphiphile coated titanium foil was found to vary inversely with the concentration of the peptide amphiphile, SEQ ID NO:1, in the coating. Specifically, 0.05% SEQ ID NO:1 solutions dried on the titanium foil surface resulted in slightly greater hydroxyapatite crystal formation than 0.1% SEQ ID NO:1 solutions dried onto titanium foil surfaces.

EXAMPLE 8

Figure 11:
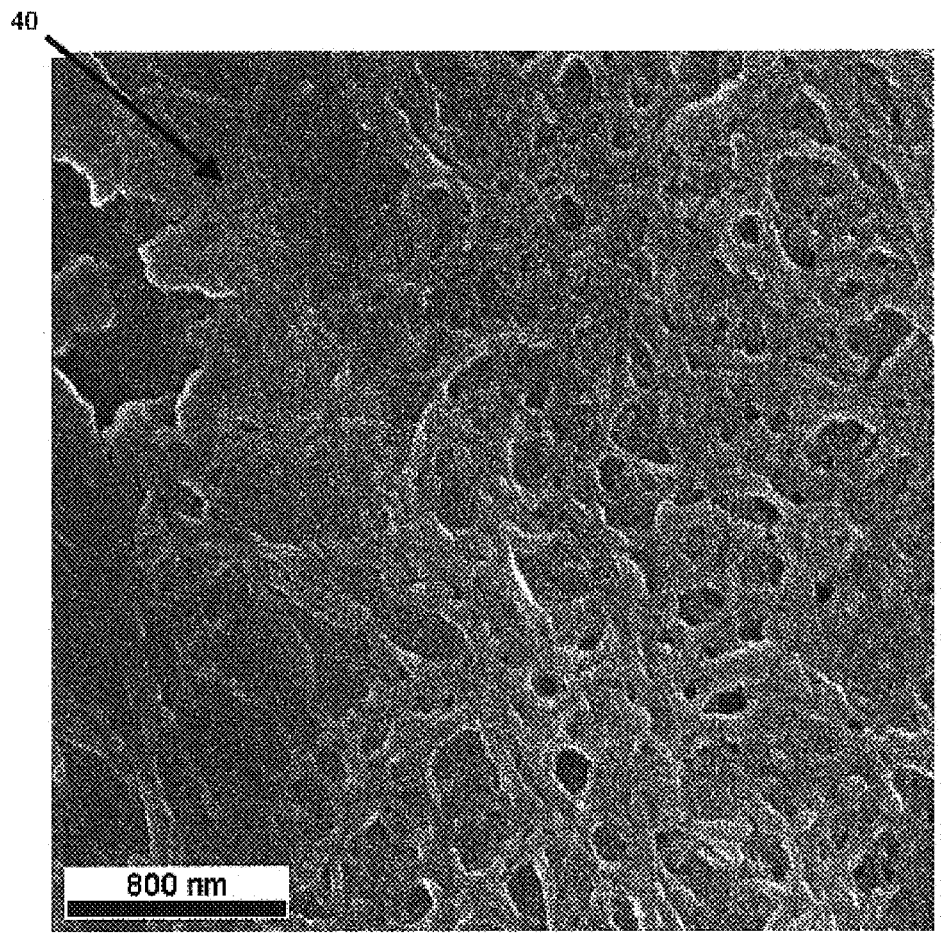
FIG. 11 is an SEM of hydroxyapatite-mineralized self assembled nanofibers, SEQ ID NO:1 on a titanium surface.

This example illustrates hydroxyapatite mineralization of a titanium surface coating of self assembled peptide amphiphiles having an SSDSD, SEQ ID NO:25, peptide sequence. 1 mL of 1 mg/mL solution of SSDSD-PA, SEQ ID NO:25, was treated with by addition of 25 mL of 200 mM $CaCl_2$ to form PA nanofibers. Titanium foils were subsequently dipped into this nanofiber suspension and excess liquid was wicked from the foil, leaving a thin film of peptide amphiphile, SEQ ID NO:1, suspension on the foil surface. This film was dried onto the foil surfaces by vacuum desiccation. The foil was subsequently treated with 2 mL of 2 mM $CaCl_2$, 2 mM b-glycerolphosphate, supplemented with 20 mL of 2 mg/mL alkaline phosphatase. Samples were treated in this solution for 7 days. The SEM in FIG. 11 reveals hydroxyapatite-mineralized fibers on the titanium surface. The coarsely mineralized nanofiber matrix on the right side of FIG. 11 is seen gradually thinning toward the left of FIG. 11. Unmineralized fibers are indicated in the top left of FIG. 11 by the arrow. This illustrates the biomimetic mineralization of the SSDSD, SEQ ID NO:25, nanofibers. Without wishing to be bound by theory, during the calcium-induced self-assembly, phosphorylated serines and aspartic acid residues on the nanofiber exterior are believed to have bound calcium. This calcium, displayed on the fiber exterior is appropriately available for the mineralization when exposed to free phosphates. In this biomimetic system, the phosphates are slowly introduced for mineralization only as the osteogenic enzyme alkaline phosphatase cleaves the phosphate from the b-glycerolphosphate. This gradual phosphate introduction allows for directed, templated growth of hydroxyapatite on the nanofiber surfaces.

All of the embodiments disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention.

While the principles of this invention have been described in connection with specific embodiments, it should be understood clearly that these descriptions are added only by way of example and are not intended to limit, in any way, the scope of this invention. For instance, various peptide amphiphiles have been described in conjunction with specific residues and corresponding cell adhesion, but other residues can be used herewith to promote a particular cell adhesion and tissue growth on the nanostructures prepared therefrom. Likewise, while the present invention has been described as applicable to biometric material or tissue engineering, it is also contemplated that gels or related systems of such peptide amphiphiles can be used as a delivery platform or carrier for drugs, cells or other cellular or therapeutic material incorporated therein. Other advantages and features will become apparent from the claims filed hereafter, with the scope of such claims to be determined by their reasonable equivalents, as would be understood by those skilled in the art.

What is claimed is:

1. A peptide amphiphile composition comprising:
   a hydrophobic component having a single alkyl group greater than six carbons in length; and
   a hydrophilic component selected from the group consisting of CCCCGGGSS*DS*D (SEQ ID NO:1), AAAAGGGSS*DS*D (SEQ ID NO:2), SLSLGGGSS*DS*D (SEQ ID NO:3), CCCCGGGS*S*DS*D (SEQ ID NO:4), AAAAGGGS*S*DS*D (SEQ ID NO:5), SLSLGGGS*S*DS*D (SEQ ID NO:6), CCCCGGGDSS*D* (SEQ ID NO:7), AAAAGGGDSS*D* (SEQ ID NO:8), SLSLGGGDSS*D* (SEQ ID NO:9), CCCCGGGDS*S*DS* (SEQ ID NO:10), AAAAGGGDS*S*DS* (SEQ ID NO:11), SLSLGGGDS*S*DS* (SEQ ID NO:12), CCCCGGGSDS*D* (SEQ ID NO:13), AAAAGGGSDS*D* (SEQ ID NO:14), SLSLGGGSDS*D* (SEQ ID NO:15), CCCCGGGS*DS*D* (SEQ ID NO:16), AAAAGGGS*DS*D* (SEQ ID NO:17), SLSLGGGS*DS*D* (SEQ ID NO:18), CCCCGGGDS*DS*D (SEQ ID NO:19), AAAAGGGDS*DS*D (SEQ ID NO:20), and SLSLGGGDS*DS*D (SEQ ID NO:21), wherein S* is phosphorylated serine,
   wherein said hydrophilic component is covalently bonded to said hydrophobic component in said peptide amphiphile, said hydrophilic component having a net charge at physiological pH, and wherein said peptide amphiphile self-assembles to form a cylindrical micelle.

2. The peptide-amphiphile compositions of claim 1, wherein the net charge on the peptide amphiphile is positive.

3. The peptide-amphiphile compositions of claim 1, wherein the net charge on the peptide amphiphile is negative.

4. The composition of claim 3, wherein the negative net charge on the peptide amphiphile is from –4 to –7.

5. The composition of claim 3, wherein the negative net charge on the peptide amphiphile is –7 or more negative.

6. The composition of claim 1, wherein the peptide component of said peptide-amphiphile includes residue with a functional moiety capable of intermolecular covalent bond formation.

7. The composition of claim 6, wherein said residue is cysteine.

8. A peptide-amphiphile compound comprising:
   an alkyl tail greater than six carbons in length covalently bonded to a hydrophilic component selected from the group consisting of CCCCGGGSS*DS*D (SEQ ID NO:1), AAAAGGGSS*DS*D (SEQ ID NO:2), SLSLGGGSS*DS*D (SEQ ID NO:3), CCCCGGGS*S*DS*D (SEQ ID NO:4), AAAAGGGS*S*DS*D (SEQ ID NO:5), SLSLGGGS*S*DS*D (SEQ ID NO:6), CCCCGGGDSS*D* (SEQ ID NO:7), AAAAGGGDSS*D* (SEQ ID NO:8), SLSLGGGDSS*D* (SEQ ID NO:9), CCCCGGGDS*S*DS* (SEQ ID NO:10), AAAAGGGDS*S*DS* (SEQ ID NO:11), SLSLGGGDS*S*DS* (SEQ ID NO:12), CCCCGGGSDS*D* (SEQ ID NO:13), AAAAGGGSDS*D* (SEQ ID NO:14), SLSLGGGSDS*D* (SEQ ID NO:15), CCCCGGGS*DS*D* (SEQ ID NO:16), AAAAGGGS*DS*D* (SEQ ID NO:17), SLSLGGGS*DS*D* (SEQ ID NO:18), CCCCGGGDS*DS*D (SEQ ID NO:19), AAAAGGGDS*DS*D (SEQ ID NO:20), and SLSLGGGDS*DS*D (SEQ ID NO:21), wherein S* is phosphorylated serine,
   wherein the peptide-amphiphile compound self-assembles to form a cylindrical micelle.

9. The peptide-amphiphile compound of claim 8, wherein said peptide amphiphile has a positive net charge.

10. The peptide-amphiphile compound of claim 8, wherein said peptide amphiphile has a negative net charge.

11. The compound of claim 10, wherein the negative net charge on the peptide amphiphile is from –4 to –7.

12. The compound of claim 10, wherein the negative net charge on the peptide amphiphile is more negative than –7.

13. The compound of claim 10, wherein the structural peptide includes a residue with a functional moiety capable of intermolecular covalent bond formation.

14. A composition comprising:
   an aqueous solution of at least one charged peptide amphiphile, said charged peptide amphiphile having a hydrophobic segment consisting of having a single alkyl group greater than six carbons in length and a hydrophilic component selected from the group consisting of CCCCGGGSS*DS*D (SEQ ID NO:1), AAAAGGGSS*DS*D (SEQ ID NO:2), SLSLGGGSS*DS*D (SEQ ID NO:3), CCCCGGGS*S*DS*D (SEQ ID NO:4), AAAAGGGS*S*DS*D (SEQ ID NO:5), SLSLGGGS*S*DS*D (SEQ ID NO:6), CCCCGGGDSS*D* (SEQ ID NO:7), AAAAGGGDSS*D* (SEQ ID NO:8), SLSLGGGDSS*D* (SEQ ID NO:9), CCCCGGGDS*S*DS* (SEQ ID NO:10), AAAAGGGDS*S*DS* (SEQ ID NO:11) SLSLGGGDS*S*DS* (SEQ ID NO:12), CCCCGGGSDS*D* (SEQ ID NO:13), AAAAGGGSDS*D* (SEQ ID NO:14), SLSLGGGSDS*D* (SEQ ID NO:15), CCCCGGGS*DS*D* (SEQ ID NO:16), AAAAGGGS*DS*DS* (SEQ ID NO:17), SLSLGGGS*DS*DS* (SEQ ID NO:18), CCCCGGGDS*DS*D (SEQ ID NO:19), AAAAGGGDS*DS*D (SEQ ID NO:20), and SLSLGGGDS*DS*D (SEQ ID NO:21), wherein S* is phosphorylated serine, wherein said hydrophilic component is covalently bonded to said hydrophobic component in said peptide amphiphile, said peptide amphiphile having a net charge at substantially physiological pH; and an agent for inducing said charged peptide amphiphiles to self assemble into a cylindrical micelle.

15. The composition of claim 14, wherein the net charge of said peptide amphiphile is positive.

16. The composition of claim 14, wherein the net charge of said peptide amphiphile is negative.

17. The composition of claim 14 wherein the agent includes solvent removal from the peptide amphiphile solution.

18. The composition of claim 16, wherein the agent inducing self assembly is chosen from the group consisting of oppositely charged peptide amphiphiles, cations, and anions.

19. A composition comprising
one or more nanofibers formed from charged self-assembled peptide amphiphiles of claim 1, said peptide amphiphiles having a hydrophobic segment covalently bonded to a hydrophilic segment, said peptide amphiphile having a net absolute charge greater than 3 at substantially physiological pH.

20. The composition of claim 19 further including a substrate, said nanofibers covering at least a portion of said substrate.

21. The composition of claim 19 further including osteoblastic cells on said nanofibers.

22. The composition of claim 19 further including a crystalline material having a crystal axis preferentially oriented with respect to the length of said nanofiber.

23. The composition of claim 19 further including osteoblastic cells and a mineral on said nanofibers.

24. The composition of claim 19 wherein said nanofibers are preferentially oriented on at least a portion of the substrate.

25. A method of stimulating mineralization in a patient with tissue engineered material comprised of:
administering a peptide amphiphile composition of claim 1 to a site on said patient in need thereof,
said peptide amphiphile capable of stimulating mineralization of said site, said peptide amphiphile compositions having a net charge at physiological pH.

26. The method of claim 25, wherein said net charge on the peptide amphiphile is positive.

27. The method of claim 25, wherein said net charge on the peptide amphiphile is negative.

28. The method of claim 27, wherein the negative net charge on the peptide amphiphile is −4 or more negative.

29. The method of claim 27, further comprising the step of adding an agent to induce self assembly of said peptide amphiphiles at said site.

30. The method of claim 25, wherein peptide-amphiphile includes and amino acid selected from the group consisting of serine, phosphorylated serine, and aspartic acid.

31. The method of claim 25, wherein the peptide-amphiphile includes a residue with a functional moiety capable of intermolecular covalent bond formation.

32. The method of claim 31, wherein the functional moiety is cysteine.

* * * * *

UNITED STATES PATENT AND TRADEMARK OFFICE
CERTIFICATE OF CORRECTION

PATENT NO.        : 7,534,761 B1  
APPLICATION NO.   : 10/645304  
DATED             : May 19, 2009  
INVENTOR(S)       : Samuel I. Stupp et al.

It is certified that error appears in the above-identified patent and that said Letters Patent is hereby corrected as shown below:

On the Title Page Item (73), please change the name of the Assignee from "North Western University" to --Northwestern University--.

In column 12, line 61, please change "DEEA" to --DIEA--.

In column 15, line 10, please change "cel" to --gel,--.

Signed and Sealed this

Twentieth Day of October, 2009

David J. Kappos  
*Director of the United States Patent and Trademark Office*

SEQUENCE LISTING

```
<160> NUMBER OF SEQ ID NOS: 25

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phosphorylated Ser
<220> FEATURE:
<221> NAME/KEY: MOD_RES
<222> LOCATION: (11)..(11)
<223> OTHER INFORMATION: Phosphorylated Ser

<400> SEQUENCE: 1

Cys Cys Cys Cys Gly Gly Gly Ser Ser Asp Ser Asp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phosphorylated Ser
<220> FEATURE:
<221> NAME/KEY: MOD_RES
<222> LOCATION: (11)..(11)
<223> OTHER INFORMATION: Phosphorylated Ser

<400> SEQUENCE: 2

Ala Ala Ala Ala Gly Gly Gly Ser Ser Asp Ser Asp
1               5                   10

<210> SEQ ID NO 3
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phosphorylated Ser
<220> FEATURE:
<221> NAME/KEY: MOD_RES
<222> LOCATION: (11)..(11)
<223> OTHER INFORMATION: Phosphorylated Ser

<400> SEQUENCE: 3

Ser Leu Ser Leu Gly Gly Gly Ser Ser Asp Ser Asp
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Phosphorylated Ser
<220> FEATURE:
<221> NAME/KEY: MOD_RES
<222> LOCATION: (11)..(11)
<223> OTHER INFORMATION: Phosphorylated Ser

<400> SEQUENCE: 4

Cys Cys Cys Cys Gly Gly Gly Ser Ser Asp Ser Asp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Phosphorylated Ser
<220> FEATURE:
<221> NAME/KEY: MOD_RES
<222> LOCATION: (11)..(11)
<223> OTHER INFORMATION: Phosphorylated Ser

<400> SEQUENCE: 5

Ala Ala Ala Ala Gly Gly Gly Ser Ser Asp Ser Asp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Phosphorylated Ser
<220> FEATURE:
<221> NAME/KEY: MOD_RES
<222> LOCATION: (11)..(11)
<223> OTHER INFORMATION: Phosphorylated Ser
```

```
<400> SEQUENCE: 6

Ser Leu Ser Leu Gly Gly Gly Ser Ser Asp Ser Asp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 7

Cys Cys Cys Cys Gly Gly Gly Asp Ser Ser Asp Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 8

Ala Ala Ala Ala Gly Gly Gly Asp Ser Ser Asp Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 9

Ser Leu Ser Leu Gly Gly Gly Asp Ser Ser Asp Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (9)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 10

Cys Cys Cys Cys Gly Gly Gly Asp Ser Ser Asp Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 11

Ala Ala Ala Ala Gly Gly Gly Asp Ser Ser Asp Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 12

Ser Leu Ser Leu Gly Gly Gly Asp Ser Ser Asp Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 13

Cys Cys Cys Cys Gly Gly Gly Ser Asp Ser Asp Ser
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (10)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 14

Ala Ala Ala Ala Gly Gly Gly Ser Asp Ser Asp Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (10)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 15

Ser Leu Ser Leu Gly Gly Gly Ser Asp Ser Asp Ser
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: Phosphorylated Ser
<220> FEATURE:
<221> NAME/KEY: MOD_RES
<222> LOCATION: (10)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 16

Cys Cys Cys Cys Gly Gly Gly Ser Asp Ser Asp Ser
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic peptide

```
<220> FEATURE:
<221> NAME/KEY: MOD_RES
<222> LOCATION: (8)..(8)
<223> OTHER INFORMATION: Phosphorylated Ser
<220> FEATURE:
<221> NAME/KEY: MOD_RES
<222> LOCATION: (10)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 17

Ala Ala Ala Ala Gly Gly Gly Ser Asp Ser Asp Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phosphorylated Ser
<220> FEATURE:
<221> NAME/KEY: MOD_RES
<222> LOCATION: (10)..(10)
<223> OTHER INFORMATION: Phosphorylated Ser
<220> FEATURE:
<221> NAME/KEY: MOD_RES
<222> LOCATION: (12)..(12)
<223> OTHER INFORMATION: Phosphorylated Ser

<400> SEQUENCE: 18

Ser Leu Ser Leu Gly Gly Gly Ser Asp Ser Asp Ser
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phosphorylated Ser
<220> FEATURE:
<221> NAME/KEY: MOD_RES
<222> LOCATION: (11)..(11)
<223> OTHER INFORMATION: Phosphorylated Ser

<400> SEQUENCE: 19

Cys Cys Cys Cys Gly Gly Gly Asp Ser Asp Ser Asp
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phosphorylated Ser
<220> FEATURE:
```

```
<221> NAME/KEY: MOD_RES
<222> LOCATION: (11)..(11)
<223> OTHER INFORMATION: Phosphorylated Ser

<400> SEQUENCE: 20

Ala Ala Ala Ala Gly Gly Gly Asp Ser Asp Ser Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phosphorylated Ser
<220> FEATURE:
<221> NAME/KEY: MOD_RES
<222> LOCATION: (11)..(11)
<223> OTHER INFORMATION: Phosphorylated Ser

<400> SEQUENCE: 21

Ser Leu Ser Leu Gly Gly Gly Asp Ser Asp Ser Asp
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Dpr

<400> SEQUENCE: 22

Ser Leu Ser Leu Xaa Xaa Xaa Gly Arg Gly Asp Ser
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Leu Ser Leu
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ala Ala Ala
1

<210> SEQ ID NO 25
```

```
-continued
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Ser Asp Ser Asp
1               5
```